United States Patent
Hudnall

(10) Patent No.: US 11,252,984 B2
(45) Date of Patent: Feb. 22, 2022

(54) METHODS OF LIVER DISEASE TREATMENT

(71) Applicant: Michael Hudnall, Scottsdale, AZ (US)

(72) Inventor: Michael Hudnall, Scottsdale, AZ (US)

(*) Notice: Subject to any disclaimer, the term of this patent is extended or adjusted under 35 U.S.C. 154(b) by 380 days.

(21) Appl. No.: 15/681,529

(22) Filed: Aug. 21, 2017

(65) Prior Publication Data

US 2017/0347696 A1    Dec. 7, 2017

Related U.S. Application Data

(63) Continuation of application No. 14/688,400, filed on Apr. 16, 2015, now abandoned.

(51) Int. Cl.

| | |
|---|---|
| *A23L 33/105* | (2016.01) |
| *A23L 33/00* | (2016.01) |
| *A23L 33/10* | (2016.01) |
| *A23L 33/18* | (2016.01) |
| *A23L 33/175* | (2016.01) |
| *A23L 33/16* | (2016.01) |
| *A23L 33/15* | (2016.01) |
| *A61K 31/198* | (2006.01) |
| *A61K 31/525* | (2006.01) |

(52) U.S. Cl.
CPC ............ *A23L 33/105* (2016.08); *A23L 33/00* (2016.08); *A23L 33/10* (2016.08); *A23L 33/15* (2016.08); *A23L 33/16* (2016.08); *A23L 33/175* (2016.08); *A23L 33/18* (2016.08); *A61K 31/198* (2013.01); *A61K 31/525* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 6,461,634 B1 * | 10/2002 | Marshall | A23L 33/40 |
| | | | 424/400 |
| 6,797,729 B1 * | 9/2004 | Byrne | A61K 31/015 |
| | | | 514/455 |
| 7,078,064 B2 | 7/2006 | Zabrecky | |

(Continued)

FOREIGN PATENT DOCUMENTS

| | | |
|---|---|---|
| EP | 2342979 | 7/2011 |
| WO | 2005006890 | 1/2005 |

(Continued)

OTHER PUBLICATIONS

Mato: S-adenosylmethionine metabolism and liver disease; Ann Hepatol. Mar.-Apr. 2013; 12(2): 183-189. (Year: 2013).*

(Continued)

*Primary Examiner* — Patricia A George
(74) *Attorney, Agent, or Firm* — Lambert Shorten & Connaughton; David J. Connaughton, Jr.; Justin P. Tinger

(57) ABSTRACT

Methods for treatment of chronic liver disease and reversing liver fibrosis are provided. These treatments may be achieved using a medical food composition. The medical food is configured specifically for those having chronic liver disease to provide for specific nutritional requirements caused by the chronic liver disease. Testing of the treated patient allows for tracking of progress and to determine if the liver fibrosis is reversed.

20 Claims, 1 Drawing Sheet

---

Identify patient having chronic liver disease

Provide medical food three times daily

Monitor patient to confirm efficacy

(56) References Cited

U.S. PATENT DOCUMENTS

| | | | |
|---|---|---|---|
| 7,887,854 B2 * | 2/2011 | Bombardelli | A61K 31/353 424/725 |
| 8,197,861 B2 | 6/2012 | Zabrecky | |
| 8,679,530 B2 | 3/2014 | Guilford et al. | |
| 2005/0031651 A1 * | 2/2005 | Gervais | A61K 45/06 424/400 |
| 2005/0260285 A1 * | 11/2005 | DiMateeo-Leggio | A61K 31/375 424/725 |
| 2008/0292607 A1 * | 11/2008 | Mazzio | A61K 31/19 424/94.1 |
| 2014/0267530 A1 | 9/2014 | Booth et al. | |

FOREIGN PATENT DOCUMENTS

| | | |
|---|---|---|
| WO | 2010104595 | 9/2010 |
| WO | 2012094636 | 7/2012 |

OTHER PUBLICATIONS

Natural Remedies: published online at least by Feb. 9, 2011 at: http://web.archive.org/web/20110506160309/http://www.naturalremedies.org/wormwood/ (Year: 2011).*
Ayushveda; Piper cubeba; published online at least by May 3, 2008 at: http://web.archive.org/web/20080503194528/http://www.ayushveda.com/herbs/piper-cubeba.htm (Year: 2008).*
Genestra: Bioretic Herbal Supplement; published online at least by Oct. 25, 2014 as shown by the comments at: https://www.amazon.com/Genestra-Brands-Dandelion-Calendula-Supplement/dp/B004BPFZRI#customerReviews (Year: 2014).*
Whitaker: Whitaker Wellness Institute: Top Three Mistakes in Diabetes Treatment; published Aug. 12, 2014; http://whitakerwellness.com/2014/08/top-three-mistakes-diabetes-treatment/ (Year: 2014).*
Swanson: Full Spectrum Black Cumin Seed; published Nov. 8, 2012; http://web.archive.org/web/20121108024119/http://www.swansonvitamins.com/swanson-premium-full-spectrum-black-cumin-seed-400-mg-60-caps (Year: 2012).*
Cleveland Clinic: Grape Seed Extract: updated online at least by Feb. 9, 2013 at: http://web.archive.org/web/20130209213821/http://www.clevelandclinicwellness.com/Features/Pages/Grape-Seed-Extract.aspx (Year: 2013).*
Cleveland Clinic: Ubiquinol page: updated online at least by Feb. 9, 2013 at: http://web.archive.org/web/20130209231445/http://www.clevelandclinicwellness.com/Features/Pages/CoQ10.aspx (Year: 2013).*
Pure Formulas: n-acetyl L-carnitine; published online at least by Jan. 16, 2013 at: http://web.archive.org/web/20130116114821/http://pureformulas.com/nacetyllcarnitine-500-mg-90-capsules-by-montiff.html (Year: 2013).*
Swanson 2: Turmeric; published online at least by Sep. 16, 2012 at: http://web.archive.org/web/20120916005308/http://www.swansonvitamins.com/swanson-premium-turmeric-720-mg-240-caps (Year: 2012).*
WHF Biotin: Biotin; published online at least by May 2, 2012 at: https://web.archive.org/web/20130502124938/http://whfoods.org/genpage.php?tname=nutrient&dbid=42 (Year: 2012).*
WHF Folate: Folate; published online at least by May 2, 2012 at: https://web.archive.org/web/20130502115827/http://whfoods.org/genpage.php?tname=nutrient&dbid=63 (Year: 2012).*
WHF Selenium: Selenium; published online at least by May 2, 2012 at: http://whfoods.org/genpage.php?tname=nutrient&dbid=95 (Year: 2012).*
WHF Zinc: Zinc; published online at least by May 2, 2013 at: https://web.archive.org/web/20130502125902/http://whfoods.org/genpage.php?tname=nutrient&dbid=115 (Year: 2013).*
WHF Magnesium: Magnesium; published online at least by Oct. 31, 2013 at: https://web.archive.org/web/20131031235307/http://whfoods.org/genpage.php?tname=nutrient&dbid=75 (Year: 2013).*
WHF E: Vitamin E; published online at least buy May 2, 2013, at: https://web.archive.org/web/20130502120001/http://whfoods.org/genpage.php?tname=nutrient&dbid=111 (Year: 2013).*
WHF D: Vitamin D; published online at least buy May 2, 2013, at: https://web.archive.org/web/20130502113257/http://whfoods.org/genpage.php?tname=nutrient&dbid=110 (Year: 2013).*
WHF C: Vitamin C; published online at least buy May 2, 2013, at: https://web.archive.org/web/20130502111043/http://whfoods.org/genpage.php?tname=nutrient&dbid=109 (Year: 2013).*
WHF B6: Vitamin B6; published online at least buy May 2, 2013, at: https://web.archive.org/web/20130502121854/http://whfoods.org/genpage.php?tname=nutrient&dbid=108 (Year: 2013).*
WHF B5: pantothenic acid; published online at least by May 2, 2013 at: https://web.archive.org/web/20130701000000*/http://whfoods.org/genpage.php?tname=nutrient&dbid=87 (Year: 2013).*
Web MD: Vitamin B3; published online at least by Apr. 4, 2013 at: https://www.webmd.com/vitamins/ai/ingredientmono-924/niacin-and-niacinamide-vitamin-b3 (Year: 2013).*
WHF B2: riboflavin-B2; published online at least by May 2, 2013 as shown by the article comments at: https://web.archive.org/web/20130502104209/http://whfoods.org/genpage.php?tname=nutrient&dbid=93 (Year: 2013).*
WHF B1: thiamin-B1; published online at least by May 2, 2013 at: https://web.archive.org/web/20130502120633/http://whfoods.org/genpage.php?tname=nutrient&dbid=100 (Year: 2013).*
Watanabe: Both Plasma Lysophosphatidic Acid and Serum Autotaxin Levels are Increased in Chronic Hepatitis C; Journal of Clinical Gastroenterology: Jul. 2007—vol. 41—Issue 6—p. 616-623 (Year: 2007).*
Douglas Laboratories®: online at least by Jan. 2014 as illustrated in comments by Faizan at: https://www.amazon.com/Douglas-Laboratories-Preventive-Comprehensive-Capsules/dp/B0010ZX1OG/ref=sr_1_10_a_it?ie=UTF8&qid=1488895748&sr=8-10& (Year: 2014).*
Lehmann: Circulating Lysophosphatidylcholines Are Markers of a Metabolically Benign Nonalcoholic Fatty Liver; Diabetes Care, vol. 36, Aug. 2013. (Year: 2013).*
Edward: Betaine Hydrochloride: How it helps with Digestion & Detoxification; published online by Nov. 30, 2009 at: http://web.archive.org/web/20100211142804/http://www.globalhealingcenter.com/natural-health/betaine-hydrochloride (Year: 2010).*
IFIC: International Food Information Council Foundation: Glutamate and Monosodium Glutamate: Examining the Myths; IFIC Review, published online at least by Feb. 6, 2011 at: https://web.archive.org/web/20110206180122/https://www.foodinsight.org/Content/76/Glutamate-and-Monosodium-Glutamate.pdf (Year: 2011).*
BM101: Building Muscle 101: How To Make Your Own Supplements; pupilshed online at least by Nov. 22, 2011 as verified at: http://web.archive.org/web/20111122001329/http://www.buildingmuscle101.com/how-to-make-your-own-supplements.html (Year: 2011).*
PhosCol: About PhosChol; published online by Mar. 8, 2005, as verified by: http://web.archive.org/web/20050308185800/http://www.phoschol.com/about_phoschol/ (Year: 2005).*
Thorton: Alpha lipoic acid reverses liver failure; Nutrition News; Jan. 17, 2014 at: https://www.naturalhealth365.com/liver-problems-vitamin-d-2734.html (Year: 2014).*
Challem: NAC the Super Nutrient; Better Nutrition; published Jan. 2014. (Year: 2014).*
Thompson: Dietary Supplement S-Adenosyl-I-Methionine (AdoMet) Effects on Plasma Homocysteine Levels in Healthy Human Subjects: A Double-Blind, Placebo-Controlled, Randomized Clinical Trial; J Altern Complement Med. May 2009; 15(5): 523-529. (Year: 2009).*
BLT: British Live Trust: Diet and Liver Disease; published online at least by Jan. 12, 2014 at: https://web.archive.org/web/20140112222642/https://www.britishlivertrust.org.uk/liver-information/diet-and-liver-disease/ (Year: 2014).*
Liu: Effect of Fuzheng Huayu formula and its actions against liver fibrosis; Published: Jun. 29, 2009; Chinese Medicine 2009, 4:12 doi: 10.1186/1749-8546-4-12. (Year: 2009).*
Xing: The Active Components of Fuzheng Huayu Formula and Their Potential Mechanism of Action in Inhibiting the Hepatic

(56) References Cited

OTHER PUBLICATIONS

Stellate Cells Viability—A Network Pharmacology and Transcriptomics Approach; Front. Pharmacol., May 24, 2018. (Year: 2018).*
CT: Clinical Trials: Assess the Antifibrotic Activity of Fuzheng Huayu in Chronic Hepatitis C Patients With Hepatic Fibrosis; ClinicalTrials.gov Identifier: NCT00854087; last Update: Jun. 27, 2014. (Year: 2014).*
Journal of Hepatology 2013 vol. 59 j 842-858 The metabolomic window into hepatobiliary disease Diren Beyog'lu, Jeffrey R. Idle Hepatology Research Group, Department of Clinical Research, University of Bem, Bem, Switzerland.
Dig Liver Dis. Apr. 2010;42(4):272-82. Epub Feb. 19, 2010. Practice guidelines for the diagnosis and management of nonalcoholic fatty liver disease. A decalogue from the Italian Association for the Study of the Liver (AISF) Expert Committee. Loria P, Adinolfi LE, Bellentani S, Bugianesi E, Grieco A, Fargion S, Gasbarrini A, Loguercio C, Lonardo A, Marchesini G, Marra F, Persico M, Prati D, Baroni GS; NAFLD Expert Committee of the Associazione Italiana per lo studio del Fegato.
Science May 22, 2009: vol. 324 No. 5930 pp. 1029-1033 DOI: 10.1126/sdence.1160809 Understanding the Warburg Effect: The Metabolic Requirements of Cell Proliferation Matthew G. Vander Heiden, Lewis C. Cantley, Craig B. Thompson.
Proc Natl Acad Sci U S A 104:5848-5853 (2007) Hepatitis C virus production by human hepatocytes dependent on assembly and secretion of very low-density lipoproteins. Huang H, Sun F, Owen DM, Li W, Chen Y, et al.
J Proteome Res 2011;10:2797-2806. A proton nuclear magnetic resonance metabonomics approach for biomarker discovery in non-alcoholic fatty liver disease Li H, Wang L, Yan X, Liu Q, Yu C, Wei H, et al.
J Virol 82: 5715-5724 (2008) Critical role of virion-associated cholesterol and sphingolipid in hepatitis C virus infection. Aizaki H, Morikawa K, Fukasawa M, Hara H, Inoue Y, et al.
PLoS ONE 6(8): e23641. doi:10.1371/journal.pone.0023641 2011 Metabolomic Profile of Hepatitis C Virus-Infected Hepatocytes. Roe B, Kensicki E, Mohney R, Hall WW.
J Proteome Res 2011;10:4825-4834 A comprehensive untargeted metabonomic analysis of human steatotic liver issue by RP and HILIC chromatography coupled to mass spectrometry reveals important metabolic alterations. Garcia-Canaveras JC, Donato MT, Castell JV, Lahoz A.
Metabolism 2011;60:404-413. Plasma metabolomic profile in non-alcoholic fatty liver disease. Kaihan SC, Guo L, Edmison J, Dasarathy S, McCullough AJ, Hanson RW, et al.
J Proteome Res 2010;9:4501-4512. Liquid chromatography-mass spectrometry-based parallel metabolic profiling of human and mouse model serum reveals putative biomarkers associated with the progression of non-alcoholic fatty liver disease. Barr J, Vazquez-Chantada M, Alonso C, Perez-Cormenzana M, Mayo R, Galan A, et al., Jan. 13, 2022.
Biochim Biophys Acta 2007;1771:1263-1270. Metabolomics (liver and blood profiling) in a mouse model in response to fasting: a study of hepatic steatosis. van Ginneken V, Verhey E, Poelmann R, Ramakers R, van Dijk KW, Ham L, et al.
Bioinformatics 30 2386-2388 10.1093/bioinformatics/btu301 db GSH: a database of S-glutathionylation. Chen Y. J., Lu C. T., LeeT. Y. (2014).
Hepatology 2012;56:118-129. Disruption of phospholipid and bile acid homeostasis in mice with non-alcoholic steatohepatitis. Tanaka N, Matsubara T, Krausz KW, Patterson AD, Gonzalez FJ.
J Viral Hepat. Feb. 2013;20(2):95-102. Epub Aug. 3, 2012. Serum bile acid levels as a predictor for the severity of liver fibrosis in patients with chronic hepatitis C. Shlomai A, Halfon P, Goldiner I, Zelber-Sagi S, Halpern Z, Oren R, Bruck R.
J Biol Chem. Jun. 11, 2010;285(24):18528-36. Epub Apr. 15, 2010. Specific contribution of methionine and choline in nutritional non-alcoholic steatohepatitis: impact on mitochondrial S-adenosyl-L-methionine and glutathione. Caballero F, Fernández A, Matías N, Martínez L, Fucho R, Elena M, Caballeria J, Morales A, Fernández-Checa JC, García-Ruiz.
Free Radic Biol Med. Jan. 1, 2012 ;52(1):59-69. Epub Oct. 13, 2011. Role of oxidative stress in the pathogenesis of nonalcoholic steatohepatitis. Rolo AP, Teodoro JS, Palmeira CM.
Gastroenterology. Nov. 2011;141(5):1572-85. Epub Sep. 12, 2011. Alcoholic liver disease: pathogenesis and new therapeutic targets. Gao B, Bataller R.
J Gastroenterol Hepatol. Oct. 2006;21 Suppl 3:S3-6. Mitochondrial glutathione: hepatocellular survival-death switch. Garcia-Ruiz C, Fernandez-Checa JC.
J Gen Virol. May 2014;95(Pt 5):991-1004. Epub Feb. 4, 2014. 'Liver let die': oxidative DNA damage and hepatotropic viruses. Higgs MR, Chouteau P, Lerat H.
World J Gastroenterol. Mar. 21, 2014;20(11):2785-800. Establishment of chronic hepatitis C virus infection: translational evasion of oxidative defence. Chan SW.
Nutr Hosp. Mar.-Apr. 2013;28(2):241-9. Third Jesus Culebras Lecture— Molecular biology and clinical nutrition; where do we stand and where do we go? Gil A.
Food Chem Toxicol. Dec. 2013;62:292-8. Epub Aug. 27, 2013. Alleviation of alcoholic liver injury by betaine involves an enhancement of antioxidant defense via regulation of sulfur amino acid metabolism. Jung YS, Kim SJ, Kwon do Y, Ahn CW, Kim YS, Choi DW, Kim YC.
J Lipid Res. Jun. 2008;49(6):1187-94. Epub Jan. 19, 2008. Phosphatidylcholine and choline homeostasis. Li Z, Vance DE.
Free Radic Biol Med. Jan. 15, 2010;48(2):357-71. Epub Nov. 13, 2009. Loss of Nrf2 markedly exacerbates nonalcoholic steatohepatitis. Chowdhry S, Nazmy MH, Meakin PJ, Dinkova-Kostova AT, Walsh SV, Tsujita T, Dillon JF, Ashford ML, Hayes JD.
Lipids Health Dis. Sep. 7, 2012;11:110. Toxicity of oxidized phospholipids in cultured macrophages. Stemmer U, Dunai ZA, Koller D, Pürstinger G, Zenzmaier E, Deigner HP, Aflaki E, Kratky D, Hermetter A.
PLoS One. Jul. 1, 2014;9(7):e100627. eCollection 2014. L-camitine prevents progression of non-alcoholic steatohepatitis in a mouse model with upregulation of mitochondrial pathway. Ishikawa H, Takaki A, Tsuzaki R, Yasunaka T, Koike K, Shimomura Y, Seki H, Matsushita H, Miyake Y, Ikeda F, Shiraha H, Nouso K, Yamamoto K.
J Nutr. Mar. 2014; 144(3):252-7. Epub Dec. 24, 2013. Choline supplementation protects against liver damage by normalizing cholesterol metabolism in Pemt/Ldlr knockout mice fed a high-fat diet. Al Rajabi A, Castro GS, da Silva RP, Nelson RC, Thiesen A, Vannucchi H, Vine DF, Proctor SD, Field CJ, Curtis JM, Jacobs RL.
Crit Rev Food Sci Nutr. 2013;53(7):706-21. Dietary intake of natural antioxidants: vitamins and polyphenols. Landete JM.
Biophys J. Mar. 2004; 86(3): 1345-1356 Complexation of Phosphatidylcholine Lipids with Cholesterol Sagar A. Pandit, David Bostick, and Max L. Berkowitz.
FEBS Journal vol. 278, Issue 6, pp. 941-954, Apr. 2011 Mitochondrial oxidative stress causes mitochondrial fragmentation via differential modulation of mitochondrial fission-fusion proteins Shengnan Wu, Feifan Zhou, Zhenzhen Zhang andDa Xing.
Alcohol. Jan.-Feb. 1997;14(1):39-44. Zinc, copper, manganese, and iron in chronic alcoholic liver disease. Rodríguez-Moreno F, González-Reimers E, Santolaria-Fernández F, Galindo-Martín L, Hernandez-Torres O, Batista-López N, Molina-Perez M.
Alcohol Clin Exp Res. Jul. 2014;38(7):1982-92. Epub May 21, 2014. Dietary nicotinic acid supplementation ameliorates chronic alcohol-induced fatty liver in rats Li Q, Xie G, Zhang W, Zhong W, Sun X, Tan X, Sun X, Jia W, Zhou Z.
Am J Physiol Gastrointest Liver Physiol. Feb. 15, 2014;306(4):G320-7. Epub Dec. 19, 2013. Therapeutic role of niacin in the prevention and regression of hepatic steatosis in rat model of nonalcoholic fatty liver disease. Ganji SH, Kukes GD, Lambrecht N, Kashyap ML, Kamanna VS.
J Nutr Biochem. Aug. 2013;24(8):1520-8 Epub Mar. 1, 2013. Protection of nicotinic acid against oxidative stress-induced cell

(56) References Cited

OTHER PUBLICATIONS death in hepatocytes contributes to its beneficial effect on alcohol-induced liver injury in mice. Dou X, Shen C, Wang Z, Li S, Zhang X, Song Z.
J Ethnopharmacol. Jun. 3, 2013;147(3):662-70. Epub Mar. 30, 2013. Aqueous extract of Artemisia capillaris exerts hepatoprotective action in alcohol-pyrazole-fed rat model. Choi MK, Han JM, Kim HG, Lee JS, Lee JS, Wang JH, Son SW, Park HJ, Son CG.
Int Immunopharmacol. Jan. 2013;15(1):106-13. Epub Nov. 8, 2012. Potential antioxidant properties and hepatoprotective effects of an aqueous extract formula derived from three Chinese medicinal herbs against CCl(4)-induced liver injury in rats. Yang CC, Fang JY, Hong TL, Wang TC, Zhou YE, Lin TC.
Nutr Res. Apr. 2008;28(4):270-7. Hepatoprotective effects of Artemisiae capillaris herba and Picrorrhiza rhizoma combinations on carbon tetrachloride-induced subacute liver damage in rats. Lee HS, Kim HH, Ku SK.
Int J Mol Med. May 2004;13(5):717-20. The aqueous extract from Artemisia capillaris Thunb. inhibits lipopolysaccharide-induced inflammatory response through preventing NF-kappaB activation in human hepatoma cell line and rat liver. Hong SH, Seo SH, Lee JH, Choi BT.
J Med Food. 2006 Fall;9(3):342-7. A water extract of Artemisia capillaris prevents 2,2'-azobis(2-amidinopropane) dihydrochloride-induced liver damage in rats. Han KH, Jeon YJ, Athukorala Y, Choi KD, Kim CJ, Cho JK, Sekikawa M, Fukushima M, Lee CH.
Arch Pharm Res. Sep. 2011;34(9):1561-9. Epub Oct. 6, 2011. Inhibition of 5-lipoxygenase and skin inflammation by the aerial parts of Artemisia capillaris and its constituents. Kwon OS, Choi JS, Islam MN, Kim YS, Kim HP.
J Ethnopharmacol. Mar. 6, 2012; 140(1): 179-85. Epub Jan. 14, 2012. PMID: 22265746 Antifibrotic effects of Artemisia capillaris and Artemisia iwayomogi in a carbon tetrachloride-induced chronic hepatic fibrosis animal model. Wang JH, Choi MK, Shin JW, Hwang SY, Son CG.
J Food Sci. Nov.-Dec. 2011;76(9):T207-11. Epub Oct. 4, 2011. PMID: 22416729 Comparative study of the hepatoprotective efficacy of Artemisia iwayomogi and Artemisia capillaris on ethanol-administered mice. Lee HI, Seo KO, Yun KW, Kim MJ, Lee MK.
Redox Rep. 2004;9(2):105-10. Antioxidant efficacy of black pepper (*Piper nigrum* L.) and piperine in rats with high fat diet induced oxidative stress Vijayakumar RS1, Surya D, Nalini N.
Phytomedicine. Feb. 2006; 13(3):196-8. Epub Jun. 24, 2005. Inhibition of CCl4-induced liver fibrosis by Piper longum Linn. Christina AJ, Saraswathy GR, Robert SJ, Kothai R, Chidambaranathan N, Nalini G, Therasal RL.
Pharm Biol. Aug. 2012;50(8):962-7. Epub Apr. 12, 2012. Hypolipidemic effects of a new piperine derivative GB-N from Piper longum in high-fat diet-fed rats. Bao L, Bai S, Borijihan G.
Indian J Exp Biol. Mar. 2009;47(3):186-92. Protective effect of Piper longum Linn. on monosodium glutamate induced oxidative stress in rats. Thomas M, Sujatha KS, George S.
Toxicol Appl Pharmacol. Jun. 1997;144(2):279-86. Antioxidative and protective properties of extracts from leaves of the artichoke (*Cynara scolymus* L.) against hydroperoxide-induced oxidative stress in cultured rat hepatocytes. Gebhardt R.
J Pharmacol Exp Ther. Sep. 1998;286(3):1122-8. Inhibition of cholesterol biosynthesis in primary cultured rat hepatocytes by artichoke (*Cynara scolymus* L.) extracts. Gebhardt R.
Nutr Cancer. 2008;60(2):276-83. Antioxidative and apoptotic properties of polyphenolic extracts from edible part of artichoke (*Cynara scolymus* L.) on cultured rat hepatocytes and on human hepatoma cells. Miccadei S, Di Venere D, Cardinali A, Romano F, Durazzo A, Foddai MS, Fraioli R, Mobarhan S, Maiani G.
Biol Trace Elem Res. Jun. 2010;135(1-3):264-74. Epub Aug. 4, 2009. Effect of artichoke leaf extract on hepatic and cardiac oxidative stress in rats fed on high cholesterol diet. Küçükgergin C, Aydin AF, Ozdemirler-Erata G, Mehmetçik G, Koçak-Toker N, Uysal M.

Alcohol Clin Exp Res. 2008;32:1525-1534. Emerging role of epigenetics in the actions of alcohol. Shukla SD, Velazquez J, French SW, et al.
Annu Rev Nutr. 2008;28:273-293. Methionine metabolism and liver disease. Mato JM, Martinez-Chantar ML, Lu SC.
Hepatology. 2010;51:932-941. Epigenetic regulation of hepatic endoplasmic reticulum stress pathways in the ethanol fed cystathionine beta synthase-deficient mouse. Esfandiari F, Medici V, Wong DH, et al.
J Lab Clin Med. Sep. 1981;98(3):417-24. Ethanol-induced lipid peroxidation: potentiation by long-term alcohol feeding and attenuation by methionine. Shaw S, Jayatilleke E, Ross WA, Gordon ER, Leiber CS.
Am J Physiol Gastrointest Liver Physiol. 2009;296:G1047-G1053. Role of SIRT1 in regulation of LPS- or two ethanol metabolites-induced TNF-alpha production in cultured macrophage cell lines. Shen Z, Ajmo JM, Rogers CQ, et al.
Gastroenterology. Feb. 2002;122(2):366-75. Mitochondrial injury, oxidative stress, and antioxidant gene expression are induced by hepatitis C virus core protein. Okuda M, Li K, Beard MR, Showalter LA, Scholle F, Lemon SM, Weinman SA.
Exp Mol Pathol. Oct. 2004;77(2):121-32. Oxidative stress in viral hepatitis and AIDS. Stehbens WE.
J Nutr. May 1997;127(5 Suppl):962S-965S. Oxidants and antioxidants in viral diseases: disease mechanisms and metabolic regulation. Peterhans E.
J Hepatol. Jun. 2002;36(6):805-11. Oxidative stress in chronic hepatitis C: not just a feature of late stage disease. Jain SK, Pemberton PW, Smith A, McMahon RF, Burrows PC, Aboutwerat A, Warnes TW.
J Virol. Jul. 2006;80(14):7199-207. Hepatitis C virus triggers mitochondrial permeability transition with production of reactive oxygen species, leading to DNA damage and STAT3 activation. Machida K, Cheng KT, Lai CK, Jeng KS, Sung VM, Lai MM.
J Biol Chem. Nov. 11, 2005;280(45):37481-8. Epub Sep. 8, 2005. Hepatitis C virus core protein inhibits mitochondrial electron transport and increases reactive oxygen species (ROS) production. Korenaga M, Wang T, Li Y, Showalter LA, Chan T, Sun J, Weinman SA.
J Gastroenterol Hepatol. Oct. 2006;21 Suppl 3:S34-7. Causes and consequences of mitochondrial reactive oxygen species generation in hepatitis C. Wang T, Weinman SA.
Int J Mol Med. Jul. 1998;2(1):51-6. Low levels of serum acylcarnitine in chronic fatigue syndrome and chronic hepatitis type C, but not seen in other diseases. Kuratsune H, Yamaguti K, Lindh G, Evengard B, Takahashi M, Machii T, Matsumura K, Takaishi J, Kawata S, Långström B, Kanakura Y, Kitani T, Watanabe Y.
J Virol 82: 5715-5724 (2008) Critical role of virion-associated cholesterol and sphingolipid in hepatitis C virus infection. Aizak H, Morikawa K, Fukasawa M, Hara H, Inoue Y, et al.
J Virol. Aug. 2007;81(15):8122-30. Epub May 16, 2007. Hepatitis C virus induces proteolytic cleavage of sterol regulatory element binding proteins and stimulates their phosphorylation via oxidative stress. Waris G, Felmlee DJ, Negro F, Siddiqui A.
Cell, vol. 147, Issue 4, 840-852, Oct. 27, 2011 A Conserved SREBP-1/Phosphatidylcholine Feedback Circuit Regulates Lipogenesis in Metazoans Amy K Walker, et al.
Gut 59: 1279-1287. (2010) Abnormalities of lipid metabolism in hepatitis C virus infection. Negro F.
Adv Pharmacol. 1997;38:601-28. Role of oxidative stress and antioxidant therapy in alcoholic and nonalcoholic liver diseases. Lieber CS.
Alcohol Alcohol. May-Jun. 2003;38(3):208-12. Polyenylphosphatidylcholine corrects the alcohol-induced hepatic oxidative stress by restoring s-adenosylmethionine. Aleynik SI, Lieber CS.
Mol Med Report. May-Jun. 2010;3(3):371-5. Zinc: A complementary factor in the treatment of chronic hepatitis C? (Review) Grüngreiff K, Reinhold D.
Chem Biol Interact. Oct. 27, 2006;163(1-2):94-112. Epub May 1, 2006. Mitochondrial function and toxicity: role of the B vitamin family on mitochondrial energy metabolism. Depeint F, Bruce WR, Shangari N, Mehta R, O'Brien PJ.

(56) References Cited

OTHER PUBLICATIONS

Am J Physiol Gastrointest Liver Physiol. Aug. 1, 2014;307(3):G313-22. Epub Jun. 12, 2014. Dysregulation of hepatic zinc transporters in a mouse model of alcoholic liver disease. Sun Q, Li Q, Zhong W, Zhang J, Sun X, Tan X, Yin X, Sun X, Zhang X, Zhou Z.
The FASEB Journal vol. 13, Jul. 1999, 1169-1183 Regulation of hepatic glutathione synthesis: current concepts and controversies Shelly C. Lu.
Theoretical Biology and Medical Modelling A mathematical model of glutathione metabolism Michael C Reed, Rachel L Thomas, Jovana Pavisic, S Jill James, Cornelia M Ulrich and H Frederik Nijhout.
J Neurochem. Jun. 2014;129(5):770-80. Epub Mar. 7, 2014. Impaired one carbon metabolism and DNA methylation in alcohol toxicity. Kruman ll1, Fowler AK.
Mol Genet Metab. Nov. 2013;110(3):388-95. Epub Sep. 17, 2013. Transcriptomic and epigenetic changes in early liver steatosis associated to obesity: effect of dietary methyl donor supplementation. Cordero P, Campion J, Milagro FI, Martinez JA.
Genes Nutr. Jan. 2013;8(1 ):105-13. Epub May 31, 2012. Dietary supplementation with methyl donors reduces fatty liver and modifies the fatty acid synthase DNA methylation profile in rats fed an obesogenic diet. Cordero P, Gomez-Uriz AM, Campion J, Milagro FI, Martinez JA.
Nutrition. Jul. 2012;28(7-8):821-4. Epub Mar. 28, 2012. The significance of folate deficiency in alcoholic and nutritional neuropathies: analysis of a case. Koike H, Hama T, Kawagashira Y, Hashimoto R, Tomita M, Iijima M, Sobue G.
Nutr Res Pract. Dec. 2011;5(6):520-6. Epub Dec. 31, 2011. Folic acid supplementation reduces oxidative stress and hepatic toxicity in rats treated chronically with ethanol. Lee SJ, Kang MH, Min H.
Hepatology. Jun. 2011;53(6):2151-2. Epub Apr. 29, 2011. Dietary supplementation with methyl donor groups could prevent nonalcoholic fatty liver. Cordero P, Campion J, Milagro Fl, Martínez JA.
Alcohol Clin Exp Res. Apr. 2009;33(4):751-8. Epub Jan. 21, 2009. Quantitative lipid metabolomic changes in alcoholic micropigs with fatty liver disease Zivkovic AM, Bruce German J, Esfandiari F, Halsted CH.
Alcohol Clin Exp Res. Jun. 2008;32(6):1049-58. Effect of transgenic extrahepatic expression of betaine-homocysteine methyltransferase on alcohol or homocysteine-induced fatty liver. Ji C, Shinohara M, Vance D, Than TA, Ookhtens M, Chan C, Kaplowitz N.
Alcohol Clin Exp Res. Nov. 2007;31(11):1934-43. Epub Sep. 11, 2007. S-adenosylmethionine attenuates oxidative liver injury in micropigs fed ethanol with a folate-deficient diet. Villanueva JA, Esfandiari F, White ME, Devaraj S, French SW, Halsted CH.
Am J Clin Nutr. Jul. 2007;86(1):14-24. Review. Role of S-adenosylmethionine, folate, and betaine in the treatment of alcoholic liver disease: summary of a symposium. Purohit V, Abdelmalek MF, Barve S, Benevenga NJ, Halsted CH, Kaplowitz N, Kharbanda KK, Liu QY, Lu SC, McClain CJ, Swanson C, Zakhar S.
Alcohol Clin Exp Res. Jul. 2007;31(7):1231-9. S-adenosylmethionine attenuates hepatic lipid synthesis in micropigs fed ethanol with a folate-deficient diet. Esfandiari F, You M, Villanueva JA, Wong DH, French SW, Halsted CH.
Semin Liver Dis. Aug. 2004;24(3):289-304. Review. Nutrition and alcoholic liver disease. Halsted CH.
Aliment Pharmacol Ther. Aug. 15, 2003;18(4):357-73. Review article: Nutritional therapy in alcoholic liver disease. Stickel F, Hoehn B, Schuppan D, Seitz HK.
J Am Coll Nutr. Dec. 1991; 10(6):602-32. Review. Role of S-adenosyl-L-methionine in the treatment of alcoholic liver disease: introduction and summary of the symposium. Purohit V, Russo D.
Alcohol. Jul. 2002;27(3): 151-4. Alcohol, liver, and nutrition. Lieber CS.
Indian J Physiol Pharmacol. Oct.-Dec. 2013;57(4):406-17. Impact of thiamine supplementation in the reversal of ethanol induced toxicity in rats. Vidhya A, Renjugopal V, Indira M.

Am J Clin Nutr. Dec. 1975;28(12):1377-80. Inability of chronic alcoholics with liver disease to use food as a source of folates, thiamin and vitamin B6.
J Pharm Pharmacol. May 2005;57(5):599-605. S-adenosyl-L-methionine: transcellular transport and uptake by Caco-2 cells and hepatocytes. McMillan JM, Walle UK, Walle T.
Alcohol. Jul. 2002;27(3):173-7. S-Adenosyl-L-methionine and alcoholic liver disease in animal models: implications for early intervention in human beings.
Am J Clin Nutr. Nov. 2002;76(5):1183S-7S. S-adenosyl-L-methionine: its role in the treatment of liver disorders. Lieber CS.
J Clin Invest. Sep. 1966; 45(9); 1400-1411. doi; 10.1172/JC1105448 Effects of prolonged ethanol intake in man; role of dietary adipose, and endogenously synthesized fatty acids in the pathogenesis of the alcoholic fatty liver. C S Lieber and N Spritz.
Drug Metab Rev. Oct. 2004;36(3-4);511-29. The discovery of the microsomal ethanol oxidizing system and its physiologic and pathologic role. Lieber CS.
Scand J Gastroenterol. May 1989;24(4);407-15. Effects of oral S-adenosyl-L-methionine on hepatic glutathione in patients with liver disease. Vendemiale G, Altomare E, Trizio T, Le Grazie C, Di Padova C, Salerno MT, Carrier V, Albano O.
Adv Nutr. Sep. 2011;2(5):421-7. doi: 10.3945/an.111.000661. Epub Sep. 6, 2011. Vitamin-dependent methionine metabolism and alcoholic liver disease. Halsted CH, Medici V.
J Nutr 2004;134:489-92 Glutathione metabolism and its implications for health. Wu G, Fang Y-Z, Yang S, Lupton J, Turner ND.
Cell Biol Toxicol 2003;19:355-66. Adaptation of subcellular glutathione detoxification system to stress conditions in choline-deficient diet induced rat fatty liver. Grattagliano I, Caraceni P, Portincasa P, et al.
Phytother Res. Apr. 2010;24(4):565-70. Artichoke leaf extract reduces oxidative stress and lipoprotein dyshomeostasis in rats fed on high cholesterol diet. Küskü-Kiraz Z, Mehmetçik G, Dogru-Abbasoglu S, Uysal M.
World J Gastroenterol. Apr. 28, 2013;19(16):2529-36. Effects of Nigella sativa on outcome of hepatitis C in Egypt. Barakat EM1, El Wakeel LM, Hagag RS.
Mol Biol Rep. May 2014;41(5):2827-34. Epub Jan. 29, 2014. Anti-inflammatuar and anti-oxidative effects of Nigella sativa L.: 18FDG-PEI imaging of inflammation. Entok E, Ustuner MC, Ozbayer C, Tekin N, Akyuz F, Yangi B, Kurt H, Degirmenci I, Gunes HV.
Phytother Res. Apr. 2003;17(4):299-305. Pharmacological and toxicological properties of Nigella sativa. Ali BH, Blunden G.
Int Immunopharmacol. Dec. 2005;5(13-14): 1749-70. Epub Jul. 1, 2005. Immunomodulatory and therapeutic properties of the Nigella sativa L. seed. Salem ML.
Phytomedicine. Apr. 15, 2012; 19(6):545-50. Epub Mar. 23, 2012. Curcumin prevents chronic alcohol-induced liver disease involving decreasing ROS generation and enhancing antioxidative capacity. Rong S, Zhao Y, Bao W, Xiao X, Wang D, Nussler AK, Yan H, Yao P, Liu L.
J Ethnopharmacol. Mar. 24, 2010; 128(2)1549-53. Epub Jan. 18, 2010. Curcumin alleviates ethanol-induced hepatocytes oxidative damage involving heme oxygenase-1 induction. Bao W, Li K, Rong S, Yao P, Hao L, Ying C, Zhang X, Nussler A, Liu L.
BMC Complement Altern Med. Mar. 5, 2013; 13:56. Hepatoprotective effect of ethanolic extract of Curcuma longa on thioacetamide induced liver cirrhosis in rats. Salama SM, Abdulla MA, AlRashdi AS, Ismail S, Alkiyumi SS, Golbabapour S.
Int J Mol Med. Oct. 2014;34(4):1110-6. Epub Jul. 25, 2014. Suppression of the TGF-β/Smad signaling pathway and inhibition of hepatic stellate cell proliferation play a role in the hepatoprotective effects of curcumin against alcohol-induced hepatic fibrosis. Chen N, Geng Q, Zheng J, He S, Huo X, Sun X.
Liver Int. Nov. 2009;29(10):1457-66. Pharmacological actions of curcumin in liver diseases or damage. Rivera-Espinoza Y, Muriel P.
Biosci Biotechnol Biochem. Dec. 1999;63(12):2118-22. Antioxidative effects of turmeric, rosemary and capsicum extracts on membrane phospholipid peroxidation and liver lipid metabolism in mice. Asai A, Nakagawa K, Miyazawa T.
J Food Sci. Apr. 2011;76(3):H80-9. Attenuation of fatty liver and prevention of hypercholesterolemia by extract of Curcuma longa

(56) References Cited

OTHER PUBLICATIONS through regulating the expression of CYP7A1, LDL-receptor, HO-1, and HMG-CoA reductase. Yiu WF, Kwan PL, Wong CY, Kam TS, Chiu SM, Chan SW, Chan R.
Nutrition. Sep. 2003;19(9):800-4. Oral administration of a turmeric extract inhibits erythrocyte and liver microsome membrane oxidation in rabbits fed with an atherogenic diet. Mesa MD, Aguilera CM, Ramírez-Tortosa CL, Ramírez-Tortosa MC, Quiles JL, Baró L, Martínez de Victoria E, Gil A.
Basic Clin Pharmacol Toxicol. Jan. 2006;98(1):32-7. Protection by turmeric and myrrh against liver oxidative damage and genotoxicity induced by lead acetate in mice. El-Ashmawy IM, Ashry KM, El-Nahas AF, Salama OM.
J Gastroenterol Hepatol. Jun. 2007;22(6):885-92. Grape seed extract reduces oxidative stress and fibrosis in axperimental biliary obstruction Dulundu E1, Ozel Y, Topaloglu U, Toklu H, Ercan F, Gedik N, Sener G.
Saudi J Gastroenterol. Jul.-Sep. 2010;16(3):194-7. Grape seed extract to improve liver function in patients with nonalcoholic fatty liver change. Khoshbaten M, Aliasgarzadeh A, Masnadi K, Farhang S, Tarzamani MK, Babaei H, Kiani J, Zaare M, Najafipoor F.
Am J Chin Med. 2008;36(5):861-72. Role of grape seed extract on methotrexate induced oxidative stress in rat liver. Cetin A, Kaynar L, Kocyigit I, Hacioglu SK, Saraymen R, Ozturk A, Sari I, Sagdic O.
Turk J Gastroenterol. Jun. 2008;19(2):92-8. The effect of grape seed extract on radiation-induced oxidative stress in the rat liver. Cetin A, Kaynar L, Koçyiğit I, Hacioğlu SK, Saraymen R, Öztürk A, Orhan O, Sağdiç O.
Diab Vase Dis Res. Jul. 2009;6(3):200-4. Antioxidant effects of a grape seed extract in a rat model of diabetes mellitus. Chis IC, Ungureanu MI, Marton A, Simedrea R, Muresan A, Postescu ID, Decea N.
World J Gastroenterol. Oct. 7, 2007;13(37):4947-54. Role of transmethylation reactions in alcoholic liver disease. Kharbanda KK.
Curr Opin Clin Nutr Metab Care. Jan. 2013;16(1):89-95. Methionine metabolic pathway in alcoholic liver injury. Kharbanda KK.
Semin Liver Dis. May 2009;29(2):155-65. Epub Apr. 22, 2009. Alcoholic liver disease and methionine metabolism. Kharbanda KK.
Redox Biol. Aug. 1, 2014;2:929-935. eCollection 2014. Innate immunity and cell death in alcoholic liver disease: Role of cytochrome P4502E1 Barnes MA, Roychowdhury S, Nagy LE.
Int J Clin Exp Med. Apr. 15, 2014;7(4):998-1004. eCollection 2014. Expansion of myeloid-derived suppressor cells from peripheral blood decreases after 4-week antiviral treatment in patients with chronic hepatitis C. Liu Y, She LH, Wang XY, Zhang GL, Yan Y, Lin CS, Zhao ZX, Gao ZL.
J Pharmacol Exp Ther. Dec. 2001;299(3):832-9. Arginine reverses ethanol-induced inflammatory and fibrotic changes n liver despite continued ethanol administration. Nanji AA, Jokelainen K, Lau GK, Rahemtulla A, Tipoe GL, Polavarapu R, Lalani EN.
Hepatology. Feb. 1998;27(2):377-82. Effects of L-arginine on the systemic, mesenteric, and hepatic circulation in patients with cirrhosis. Kakumitsu S, Shijo H, Yokoyama M, Kim T, Akiyoshi N, Ota K, Kubara K, Okumura M, Inoue K.
World J Surg Oncol. May 31, 2012;10:99. Effect of L-arginine supplement on liver regeneration after partial hepatectomy in rats. Kurokawa T, An J, Tsunekawa K, Shimomura Y, Kazama S, Ishikawa N, Nonami T, Sugiyama S.
Microvasc Res. Sep. 2009;78(2):206-11. Epub Jun. 30, 2009. The effect of consecutively larger doses of L-arginine on hepatic microcirculation and tissue oxygenation in hepatic steatosis. Ijaz S, Winslet MC, Seifalian AM. Rodríguez-Moreno F, González-Reimers E, Santolaria-Fernández F, Galindo-Martin L, Hemandez-Torres O, Batista-López N, Molina-Perez M.
Gastroenterol Clin Biol. Oct. 1985;9(10):664-9. [Trace elements (zinc, copper, manganese) in alcoholic cirrhosis: effect of chronic alcoholism]. [Article in French] Zarski JP, Amaud J, Dumolard L, Favier A, Rachail M.
Coll Antropol. Sep. 2006;30(3):523-8. Serum concentration of zinc, copper, manganese and magnesium in patients with liver cirrhosis. Rahelić D1, Kujundzić M, Romić Z, Brkić K, Petrovecki M.
J Nutr Biochem. Dec. 2013;24(12):2040-50. Pomegranate reverses methotrexate-induced oxidative stress and apoptosis in hepatocytes by modulating Nrf2-NF-κB pathways. Mukherjee S, Ghosh S, Choudhury S, Adhikary A, Manna K, Dey S, Sa G, Das T, Chattopadhyay S.
Front Pharmacol. 2014; 5; 151. Glutathione and mitochondria Vicent Ribas, Carmen García-Ruiz, and José C. Fernández-Checa.
Food Chem Toxicol. Aug. 8, 2014;72C:303-311. [Epub ahead of print] The berry constituents quercetin, kaempferol, and pterostilbene synergistically attenuate reactive oxygen species: Involvement of the Nrf2-ARE signaling pathway. Saw CL, Guo Y, Yang AY, Paredes-Gonzalez X, Ramirez C, Pung D, Kong AN.
J Med Food. Feb. 2014;17(2):254-61. Epub Dec. 10, 2013. The effects of α-lipoic acid on liver oxidative stress and free fatty acid composition in methionine-choline deficient diet-induced NAFLD. Stanković MN, Mladenović D, Ninković M, Ethuričić I, Sobajić S, Jorgačević B, de Luka S, Vukicevic RJ, Radosavljević TS.
Neurochem Int. Feb. 2011;58(2):190-5. Epub Nov. 27, 2010. Hyperammonemia increases the expression and activity of the glutamine/arginine transporter y+ LAT2 in rat cerebral cortex: implications for the nitric oxide/cGMP pathway. Zielińska M, Ruszkiewicz J, Hilgier W, Fręśko I, Albrecht J.
Sci Signal. Jan. 1, 2013 ;6(256):rs1. Nitric oxide regulates mitochondrial fatty acid metabolism through reversible protein S-nitrosylation. Doulias PT, Tenopoulou M, Greene JL, Raju K, Ischiropoulos H.
Biochem. Pharmacol. 64 1019-1026 10.1016/50006-2952(02)01172-3 (2002). Cellular glutathione and thiols metabolism. Dickinson D. A., Forman H. J.
Hepatology 2009;50:1827-1838. The plasma lipidomic signature of non-alcoholic steatohepatitis. Puri P, Wiest MM, Cheung O, Mirshahi F, Sargeant C, Min HK, et al.
Hepatology. Feb. 2006;43(2 Suppl 1 ):S99-S112. Nonalcoholic fatty liver disease: from steatosis to cirrhosis. Farrell GC, Larter CZ.
J Inflamm (Lond) 2011;8:8. Inflammatory Signals shift from adipose to liver during high fat feeding and influence the development of steatohepatitis in mice. Stanton MC, Chen SC, Jackson JV, Rojas-Triana A, Kinsley D, Cui L, et al.
Chin Med J (Engl) 2011;124:1367-1373. A serum metabonomic study on the difference between alcohol- and HBV-induced liver cirrhosis by ultraperformance liquid chromatography coupled to mass spectrometry plus quadrupole time-of-flight mass spectrometry. Lian JS, Liu W, Hao SR, Guo YZ, Huang HJ, Chen DY, et al.
Alcohol Clin Exp Res 2009;33:751-758. Quantitative lipid metabolomic changes in alcoholic micropigs with fatty liver disease. Zivkovic AM, Bruce German J, Esfandiari F, Halsted CH.
J Chromatogr B Analyt Technol Biomed Life Sci 2011;879:2369-2375. Metabolomics study of alcohol-induced liver injury and hepatocellular carcinoma xenografts in mice. Li S, Liu H, Jin Y, Lin S, Cai Z, Jiang Y.
Toxicol Appl Pharmacol 2011;255:127-137. Lipidomic changes in rat liver after long-term exposure to ethanol. Fernando H, Bhopale KK, Kondraganti S, Kaphalia BS, Shakeel Ansari GA.
J Proteome Res 2006;5:554-561. High performance liquid chromatography-mass spectrometry for metabonomics: potential biomarkers for acute deterioration of liver function in chronic hepatitis B. Yang J, Zhao X, Liu X, Wang C, Gao P, Wang J, et al.
Acta Biochim Biophys Sin (Shanghai) 2010;42:688-698. Development and validation of a liquid chromatography-mass spectrometry metabonomic platform in human plasma of liver failure caused by hepatitis B virus. Zhang L, Jia X, Peng X, Ou Q, Zhang Z, Qiu C, et al.
Mol Cell Proteomics 2012;12:710-719. Metabolomic analysis of key regulatory metabolites in HCV-infected tree shrews. Sun H, Zhang A, Yan G, Piao C, Li W, Sun C, et al.
Science 1956;124:269-270. On respiratory impairment in cancer cells. Warburg O.

(56) References Cited

OTHER PUBLICATIONS

Nutr Res. Nov. 2013;33(11):932-41. Epub Sep. 18, 2013. Acetyl-L-carnitine and lipoic acid improve mitochondrial abnormalities and serum levels of liver enzymes in a mouse model of nonalcoholic fatty liver disease. Kathirvel E, Morgan K, French SW, Morgan TR.
Alcohol Clin Exp Res. May 1999;23(5):944-9. Prevention and treatment of liver fibrosis based on pathogenesis. Lieber CS.
Biochim Biophys Acta. Jun.-Jul. 2010;1797(6-7):1217-24. Epub Feb. 11, 2010. Cholesterol and peroxidized cardiolipin in mitochondrial membrane properties, permeabilization and cell death. Montero J1, Mari M, Colell A, Morales A, Basañez G, Garcia-Ruiz C, Fernández-Checa JC.
World J Gastroenterol. Mar. 14, 2014;20(10):2515-32. Hepatic inflammation and progressive liver fibrosis in chronic liver disease. Czaja AJ.
Life Sci. Jun. 27, 2014;107(1-2):50-8. Epub May 5, 2014. Antioxidant and anti-inflammatory effects of N-acetylcysteine against malathion-induced liver damages and immunotoxicity in rats. Lasram MM, Lamine AJ, Dhouib IB, Bouzid K, Annabi A, Belhadjhmida N, Ahmed MB, El Fazaa S, Abdelmoula J, Gharbi N.
Hepatol Res. Jun. 24, 2014. Concomitant inhibition of oxidative stress and angiogenesis by chronic hydrogen-rich saline and N-acetylcysteine treatments improves systemic, splanchnic and hepatic hemodynamics of cirrhotic rats. Lee PC, Yang YY, Huang CS, Hsieh SL, Lee KC, Hsieh YC, Lee TY, Lin HC.
Dig Dis Sci. May 6, 2014. [Epub ahead of print] Alcoholic Hepatitis: Current Management. Spengler EK, Dunkelberg J, Schey R.
World J Gastroenterol. Mar. 7, 2014;20(9):2168-75. Chronic liver inflammation: clinical implications beyond alcoholic liver disease. Park BJ, Lee YJ, Lee HR.
Am J Pathol. 2003; 163:1137-1146. A critical involvement of oxidative stress in acute alcohol-induced hepatic TNF-alpha production. Zhou Z, Wang L, Song Z, Lambert JC, McClain CJ, Kang YJ.
Alcohol Clin Exp Res. Jun. 2014;38(6):1540-9. Epub Apr. 14, 2014. Methylation and gene expression responses to ethanol feeding and betaine supplementation in the cystathionine beta synthase-deficient mouse. Medici V, Schroeder D, Woods R, LaSalle JM, Geng Y, Shibata NM, Peerson J, Hodzic E, Dayal S, Tsukamoto H, Kharbanda KK, Tillman B, French SW, Halsted CH.
Alcohol Clin Exp Res. Jun. 1993;17(3):552-5. Dietary betaine promotes generation of hepatic S-adenosylmethionine and protects the liver from ethanol-induced fatty infiltration Barak AJ, Beckenhauer HC, Junnila M, Tuma DJ.
Magnes Res. Jun. 2008;21(2):124-30. Effects of long-term dietary intake of magnesium on oxidative stress, apoptosis and ageing in rat liver. Martin H, Uring-Lambert B, Adrian M, Lahlou A, Bonet A, Demougeot C, Devaux S, Laurant P, Richert L, Berthelot A.
Am J Gastroenterol. Dec. 2008;103(12):3159-66. Epub Sep. 11, 2008. The impact of diet on liver fibrosis and on response to interferon therapy in patients with HCV-related chronic hepatitis. Loguercio C, Federico A, Masarone M, Torella R, Blanco Cdel V, Persico M.
Eur J Nutr. Oct. 2011;50(7):499-506. Epub Dec. 24, 2010. Vitamins B status and antioxidative defense in patients with chronic hepatitis B or hepatitis C virus infection. Lin CC, Liu WH, Wang ZH, Yin MC.
J Nutr Sci Vitaminol (Tokyo). Jun. 2001;47(3):188-94. Effect of vitamin B6 deficiency on the synthesis and accumulation of S-adenosylhomocysteine and S-adenosylmethionine in rat tissues. Nguyen TT, Hayakawa T, Tsuge H.
Proc Natl Acad Sci U S A. Apr. 24, 2001; 98(9): 4916-4921. Vitamin B12 and hepatitis C: Molecular biology and human pathology William B. Lott, Seyedtaghi S. Takyar, Joseph Tuppen, Darrell H. G. Crawford,II Michael Harrison, Theo P. Sloots, and Eric J. Gowans.
Eur J Nutr. Aug. 2007;46(5):293-9. Epub Jun. 14, 2007. B vitamins deficiency and decreased anti-oxidative state in patients with liver cancer. Lin CC, Yin MC.
Semin Liver Dis. Nov. 2011;31(4):387-98. Epub Dec. 21, 2011. Classical and emerging roles of vitamin D in hepatitis C virus infection. Gutierrez JA, Parikh N, Branch AD.
World J Gastroenterol. Aug. 14, 2005;11(30):4697-702. Blood micronutrient, oxidative stress, and viral load in patients with chronic hepatitis C. Ko WS, Guo CH, Yeh MS, Lin LY, Hsu GS, Chen PC, Luo MC, Lin CY.
Quad Sclavo Diagn. Mar. 1987;23(1):12-7. Serum levels of magnesium in hepatic cirrhosis. Pasqualetti P, Casale R, Colantonio D, Di Lauro G, Festuccia V, Natali L, Natali G.
Oxid Med Cell Longev. 2014;2014:541230. Epub May 4, 2014. Oxidative stress and mitochondrial dysfunction across broad-ranging pathologies: toward mitochondria-targeted clinical sliategies. Pagano G, Talamanca AA, Castello G, Cordero MD, d'Ischia M, Gadaleta MN, Pallardó FV, Petrović S, Tiano L, Zatterale A.
Mol Nutr Food Res. Jan. 2014;58(1):147-71. Epub Dec. 3, 2013. Chemoprevention of nonalcoholic fatty liver disease by dietary natural compounds. Pan MH, Lai CS, Tsai ML, Ho CT.
Gastroenterol Hepatol. Jun.-Jul. 2012;35(6):386-94. Epub May 17, 2012. Antioxidant supplementation attenuates oxidative stress in chronic hepatitis C patients. Farias MS, Budni P, Ribeiro CM, Parisotto EB, Santos CE, Dias JF, Dalmarco EM, Fröde TS, Pedrosa RC, Wilhelm Filho D.
Methods Mol Biol. 2012;837:169-79. Assay to measure oxidized and reduced forms of CoQ by LC-MS/MS. Hahn SH, Kerfoot S, Vasta V.
J Inorg Biochem. Jan. 2008; 102(1):110-8. Epub Aug. 1, 2007. Selenium supplementation increases liver MnSOD expression: molecular mechanism for hepato-protection. Shilo S, Pardo M, Aharoni-Simon M, Glibter S, Tirosh O.
Biol Trace Elem Res. Dec. 2012;150(1-3):81-90. doi: 10.1007/s12011-012-9501-y. Epub Sep. 12, 2012. Effects of mineral supplementation on liver cirrhotic/cancer male patients. Kazi TG, Kolachi NF, Afridi HI, Kazi NG, Sirajuddin, Naeemullah, Arain SS.
World J Gastroenterol. Aug. 28, 2005;11(32):4957-61. Effects of dietary supplementation with vitamin E and selenium on rat hepatic stellate cell apoptosis. Shen XH, Cheng WF, Li XH, Sun JQ, Li F, Ma L, Xie LM.
Clinics (Sao Paulo). Aug. 2014;69(8):542-6. The association of vitamin D deficiency with non-alcoholic fatty liver disease. Küçükazman M, Ata N, Dal KA, Yeniova AÖ, Kefeli AE, Basyigit S, Aktas B, Akin KO, A Ladio Lu K, Ure OS, Topal F, Nazligül YA, Beyan E, Ertugrul DT.
Scand J Clin Lab Invest. Jul. 9, 2014:1-8. Prevalence of vitamin D deficiency and insufficiency in Bulgarian patients with chronic Hepatitis C viral infection. Gerova DI, Galunska BT, Ivanova II, Kotzev IA, Tchervenkov TG, Balev SP, Svinarov DA.
J Gastroenterol Hepatol. Aug. 2013;28 Suppl 1:49-55. Vitamin D in liver diseases: from mechanisms to clinical trials. Han YP, Kong M, Zheng S, Ren Y, Zhu L, Shi H, Duan Z.
Biochim Biophys Acta. Jun. 2012;1823(6):1102-9. Epub Apr. 13, 2012. Cap-independent Nrf2 translation is part of a lipoic acid-stimulated detoxification stress response. Shay KP, Michels AJ, Li W, Kong AN, Hagen TM.
Drug Metab Rev. May 1998;30(2):245-75. alpha-Lipoic acid: a metabolic antioxidant which regulates NF-kappa B signal transduction and protects against oxidative injury. Packer L.
PlosOne Published: Jun. 6, 2013, DOI: 10.1371/journal.pone.0065455 Mitofusin 2 Protects Hepatocyte Mitochondrial Function from Damage Induced by GCDCA Yongbiao Chen, Lizhi Lv, Zhelong Jiang, Hejun Yang, Song Li, Yy Jiang.
Gastroenterol Clin Biol. Apr. 2007;31(4):415-20. Steatosis, chronic hepatitis virus C infection and homocysteine. Roblin X, Pofelski J, Zarski JP.
Int J Biochem Cell Biol. Apr. 2000;32(4):385-9. Homocysteine. Finkelstein JD, Martin JJ.
World J Gastroenterol. Jun. 21, 2014;20(23):7260-76. Cellular and molecular mechanisms in the pathogenesis of liver fibrosis: An update. Elpek GÖ.
Am J Physiol Cell Physiol. Oct. 15, 2013;305(8):C789-99. Epub Jul. 31, 2013. Cellular mechanisms of tissue fibrosis. 5. Novel insights into liver fibrosis Mallat A, Lotersztajn S.

(56) References Cited

OTHER PUBLICATIONS

J Gastroenterol Hepatol. Jul. 1999;14(7):618-33. Liver fibrogenesis and the role of hepatic stellate cells: new insights and prospects for therapy. Li D, Friedman SL.
PLoS One. Aug. 7, 2014;9(8):e 103955. eCollection 2014. Phosphatidylcholine Alteration Identified Using MALDI Imaging MS in HBV-Infected Mouse Livers and Virus-Mediated Regeneration Defects. Park ES, Lee JH, Hong JH, Park YK, Lee JW, Lee WJ, Lee JW, Kim KP, Kim KH.
J Hepatol. Dec. 2010;53(6):1085-94. Epub Aug. 11, 2010. Oral N-acetylcysteine rescues lethality of hepatocyte-specific Gclc-knockout mice, providing a model for hepatic cirrhosis. Chen Y, Johansson E, Yang Y, Miller ML, Shen D, Orlicky DJ, Shertzer HG, Vasiliou V, Nebert DW, Dalton TP.
Nutrients. Aug. 22, 2014;6(8):3336-52. Piperine Inhibits the Activities of Platelet Cytosolic Phospholipase A2 and Thromboxane A2 Synthase without Affecting Cyclooxygenase-1 Activity: Different Mechanisms of Action Are Involved in the Inhibition of Platelet Aggregation and Macrophage Inflammatory Response. Son DJ, Akiba S, Hong JT, Yun YP, Hwang SY, Park YH, Lee SE.
Front Pharmacol. Aug. 26, 2014;5:196. eCollection 2014. Glutathione: new roles in redox signaling for an old antioxidant. Aquilano K, Baldelli S, Cinolo MR.
Klin Wochenschr. Jul. 3, 1979;57(13):661-5. Activities of urea-cycle enzymes in chronic liver disease. Maier KP, Talke H, Gerok W.
Biochemical Journal Oct. 1985; 230(3):675-81. Article: Decreased urea synthesis in cafeteria-diet-induced obesity in the rat. T Barber, J R Viña, J Cabo.
Pharmacological Reports 2011, 63, 643-659 ISSN 1734-1140 Review Activity of essential phospholipids (EPL) from soybean in liver diseases Karl-Josef Gundermann, Ann Kuenker, Erwin Kuntz, Marek DroŸdzik.
Ili. V, Begic-Janeva A: Treatment of HBsAg positive chronic active hepatitis. Efficacy of "essential" phospholipids (German) Med Welt, 1991, 42, 523-525.
J Biol Chem. Sep. 15, 1986;261(26):12114-9. Antioxidant protection of phospholipid bilayers by alpha-tocopherol. Control of alpha-tocopherol status and lipid peroxidation by ascorbic acid and glutathione. Liebier DC, Kling DS, Reed DJ.
Liver, 2005, 10, 5-7. Polyunsaturated phosphatidylcholine (Essentiale) in the treatment of alcoholic liver disease and fatty liver disease, a systematic review (Chinese) Hu G, Liu K, Zhao L.
Chin J Evidence-Based Med, 2005, 5, 543-548 Polyunsaturated phosphatidylcholine (Essentiale) for chronic hepatitis, a systematic review (Chinese) Hu G-P, Liu K, Wang S, Tang H, Zhao L-S.
Hepatology, 1990, 12, 1390-1398. Attenuation of alcohol-induced hepatic fibrosis by polyunsaturated lecithin. Lieber CS, DeCarli LM, Mak KM, Kim C-I, Leo MA.
Gastroenterology, 1994, 106, 152-159. Phosphatidylcholine protects against fibrosis and cirrhosis in the baboon. Lieber CS, Robins SJ, Li J, DeCarli LM, Mak KM, Fasulo JM, Leo MA.
J Hepatol, 1996, 24, 604-613. Polyenylphosphatidylcholine attenuates non-alcoholic hepatic fibrosis and accelerates its regression. Ma X, Zhao J, Lieber CS.
Proc Soc Exp Biol Med. Jun. 1992;200(2):271-6. Interactions among antioxidants in health and disease: vitamin E and its redox cycle. Packer L.
Biochem Pharmacol. Dec. 1, 1990,40(11):2403-13. Mechanisms of stabilization of biomembranes by alpha-tocopherol. The role of the hydrocarbon chain in the inhibition of lipid peroxidation. Kagan VE, Serbinova EA, Bakalova RA, Stoytchev TS, Erin AN, Prilipko LL, Evstigneeva RP.
Biochem Biophys Res Commun. Jun. 29, 1990;169(3):851-7. Antioxidant effects of ubiquinones in microsomes and mitochondria are mediated by tocopherol recycling Kagan V, Serbinova E, Packer L.
Ann N Y Acad Sci. Sep. 30, 1992;669:7-20. Antioxidant functions of vitamins. Vitamins E and C, beta-carotene, and other carotenoids. Sies H1, Stahl W, Sundquist AR.
Free Radic Biol Med. 1990;8(3):281-91. The physiological role of zinc as an antioxidant. Bray TM, Bettger WJ.
J Nutr. May 2000;130(5S Suppl):1447S-54S. The antioxidant properties of zinc. Powell SR.
Free Radic. Res. 39 573-580 10.1080/10715760500072172 (2005). Regulation of protein function by glutathionylation. Ghezzi P.
Biochim. Biophys. Acta 1830 3165-3172 10.1016/j.bbagen.2013.02.009 (2013) Protein glutathionylation in health and disease Ghezzi P.
Free Radic. Biol. Med. 39 345-354 10.1016/j.freeradbiomed.2005.03.022 (2005) Activation of c-Jun-N-terminal kinase s required for apoptosis triggered by glutathione disulfide in neuroblastoma cells. Filomeni G., Aquilano K., Civitareale P., Rotilio G., Ciriolo M. R.
Biol. Chem. 390 191-214 10.1515/BC.2009.033 (2009). Glutathione dysregulation and the etiology and progression of human diseases. Ballator N., Krance S. M., Notenboom S., Shi S., Tieu K., Hammond C. L.
Ann. N. Y. Acad. Sci. 1019 346-349 10.1196/annals. 1297.059 (2004). Glutathione metabolism during aging and in Alzheimer disease. Liu H., Wang H., Shenvi S., Hagen T. M., Liu R. M.
Free Radic. Biol. Med. 30 1191-1212 10.1016/50891-5849(01)00480-4 (2001). Redox environment of the cell as viewed through the redox state of the glutathione disulfide/glutathione couple Schafer F. Q., Buettner G. R.
Shock. Aug. 2008;30(2):197-205. doi: 10.1097/shk.0b013e318160f417. S-adenosyl-L-methionine attenuates oxidative stress and hepatic stellate cell activation in an ethanol-LPS-induced fibrotic rat model. Karaa A, Thompson KJ, McKillop IH, Clemens MG, Schrum LW.
Chem. Phys. Lipids 45 143-169 10.1016/0009-3084(87)90064-8 (1987). Glutathione depleting agents and lipid peroxidation. Comporti M.
J. Biol. Chem. 222 193-214. The function of cytidine coenzymes in the biosynthesis of phospholipides. Kennedy E. P., and S. B. Weiss. 1956.
Annu. Rev. Biochem. 26 119-148 1957. Metabolism of lipides. . Kennedy E. P.
Phosphatidylcholine Metabolism. D. E. Vance, editor. CRC Press, Boca Raton, FL. 1-9. 1989. Discovery of the pathways for the biosynthesis of phosphatidylcholine. Kennedy, E. P.
Cytokine. Mar. 2007;37(3):212-7. Epub May 7, 2007. Glutathione depletion is involved in the inhibition of procollagen alpha1(l) mRNA levels caused by TNF-alpha on hepatic stellate cells. Varela-Rey M, Fontán-Gabás L, Blanco P, López-Zabalza MJ, Iraburu MJ.
Hepatology. Feb. 2006;43(2 Suppl 1):S82-8. Reversal of hepatic fibrosis—fact or fantasy? Friedman SL1, Bansal MB.
Aliment Pharmacol Ther. Nov. 15, 2008;28(10):1175-87. Epub Aug. 30, 2008. Systematic review: hepatic fibrosis—regression with therapy. Zois CD1, Baltayiannis GH, Karayiannis P, Tsianos EV.
Best Pract Res Clin Gastroenterol. Apr. 2011;25(2):305-17. Antifibrogenic strategies and the regression of fibrosis. Kisseleva T1, Brenner DA.
Hepatitis C Hepatitis B [228], NASH [229] autoimmune hepatitis [230], and secondary biliary fibrosis [231].
Arthur MJ. Reversibility of liver fibrosis and cirrhosis following treatment for hepatitis C. Gastroenterology. 2002;122:1525-1528.
Kweon YO, Goodman ZD, Dienstag JL, et al. Decreasing fibrogenesis: an immunohistochemical study of paired liver biopsies following lamivudine therapy for chronic hepatitis B. J Hepatol. 2001,35:749-755.
Dixon JB, Bhathal PS, Hughes NR, O'Brien PE. Nonalcoholic fatty liver disease: Improvement in liver histological analysis with weight loss Hepatology. 2004;39:1647-1654.
Czaja AJ, Carpenter HA. Decreased fibrosis during corticosteroid therapy of autoimmune hepatitis. J Hepatol. 2004;40:646-652.
Hammel P, Couvelard A, O'Toole D, et al. Regression of liver fibrosis after biliary drainage in patients with chronic pancreatitis and stenosis of the common bile duct N Engl J Med 2001;344:418-423.
Ramachandran P, Iredale JP. Reversibility of liver fibrosis. Ann Hepatol. 2009;8:283-291.

\* cited by examiner

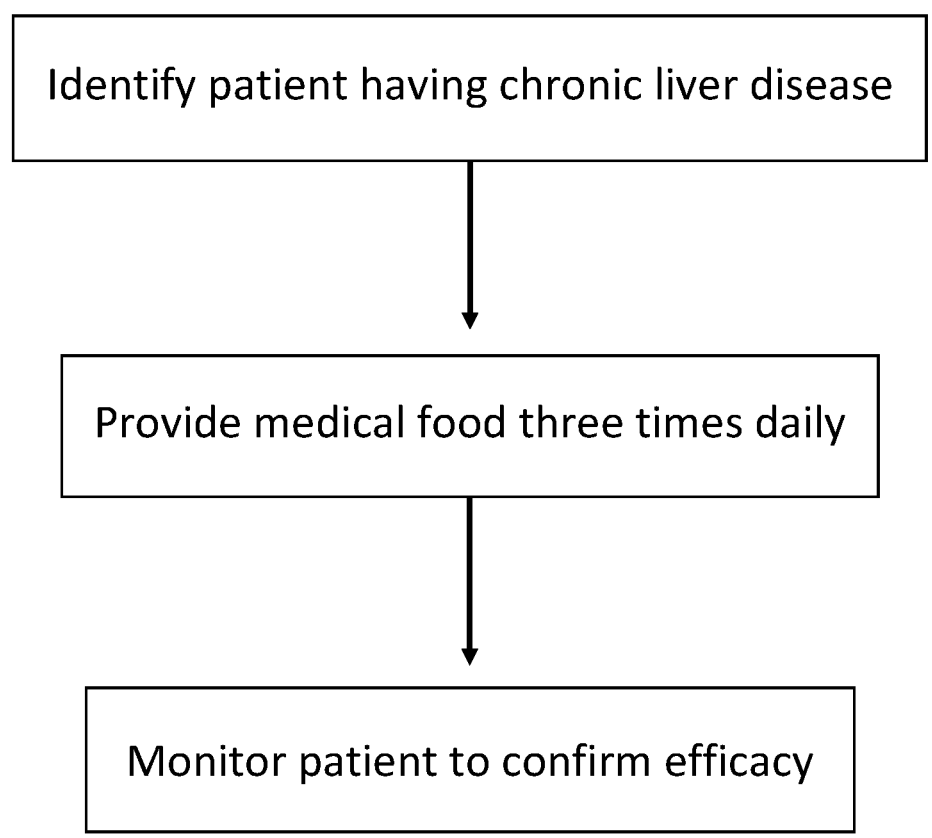

METHODS OF LIVER DISEASE TREATMENT

BACKGROUND

The present invention relates to medical food compositions. More particularly, the present invention relates to a medical food for patients with Chronic Liver Disease specifically formulated to fulfill specific, distinctive dietary requirements of patients with chronic liver disease. In some embodiments, the medical food contemplated herein may reverse liver fibrosis.

Chronic Liver Disease (CLD) continues to rise in countries worldwide and it is a growing problem in the US in particular. The spectrum of CLD include, but is not limited to the predominate hepatic diseases—hepatitis C (HCV) and hepatitis B (HBV) viruses, non-alcoholic fatty liver disease (NAFLD) with associated non-alcoholic steatohepatitis (NASH), and alcoholic liver disease (ALD). All of these chronic liver conditions may lead to cirrhosis and hepatocellular carcinoma (HCC). While new HCV antiviral drugs are effective at eliminating the virus in 90% of HCV-infected patients that receive them, the expense of these new drugs has limited availability in the short term. Effective prophylactic HBV vaccines have reduced the risk of HBV in this country, but HBV is still a worldwide epidemic and antiviral medications are only prescribed in chronic at-risk HBV cases. Further, while we have made medical advances in HCV antivirals and HBV vaccines, NAFLD and NASH are on the rise in this country. The rampant epidemic of obesity has led to significant rates of NAFLD affecting 17% to 33% of individuals in the United States. It is estimated that six million people have progressed to NASH. It is currently projected that NASH patients will soon overtake HCV patients in the number of liver transplantations performed every year.

CLD has been the subject of extensive studies over the decades that add to our collective knowledge of hepatic fibrogenesis, liver disease and the various means by which CLD disrupts metabolism. CS Leiber was a pioneer in these areas, performing many animal studies involving ALD, steatosis, cirrhosis and the administration of phosphatidylcholine (PC) and/or SAMe to correct CLD-associated metabolic disruptions and hepatic fibrosis.

In a historical context, ten years ago valuable new types of studies called metabolomic studies were begun and started being reported in the literature. Since that time metabolomic studies have become established as mainstream science. Metabolomics involves a comparative analysis of global metabolic profiles between two or more samples. Extensive metabolomic studies have been performed on hepatobiliary diseases over the last ten years. Metabolomic studies confirmed the findings of past CLD studies documenting various disruptions of metabolism, including GSH metabolism, PC metabolism, SAMe/homocysteine metabolism, one-carbon metabolism, redox homeostasis, etc. seen in all patients with CLD.

Metabolomic studies have also provided new and valuable insights into CLD pathology, especially because these studies specifically identify metabolic alterations and core metabolic phenotype (CMP) changes associated with CLD. Metabolomics involve high-throughput analytic chemistry combined with multivariate data analysis to compile an unbiased, and often extensive profile of small metabolites from various samples including animal models, in-vitro hepatocytes, live human samples, serum, plasma, etc. The focus of Metabolomic studies on the liver is at least partly due to the fact that no other organ in the body has nearly as much metabolic activity as the liver, so it is an obvious choice as an organ to study changes in the metabolome associated with disease states, in this case CLD.

The hepatic metabolome consists of a very complex collection of small-molecule (<1.5 kDa) lipid and water-soluble metabolites that interact in complex ways. The flux of these metabolites provides information about genomic, proteomic and transcriptomic activity that correlate with both normal and disease-altered hepatic metabolism. Extensive Metabolomic analyses on CLD samples over the last decade have identified specific metabolic/phenotypic alterations associated with various forms of hepatobiliary disease states. Not surprising, Leiber identified many of these same CLD-disrupted pathways in his many historic liver disease studies.

Strikingly, hepatic metabolic alterations to the phenotype associated with CLD all exhibit a similar, almost identical global profile. In other words, CLD progresses in similar patterns defined by similar epigenetic alterations in metabolic activity, regardless of the etiology of the disease. The profile of these combined alterations make up a specific "Core Metabolic Phenotype" (CMP) in patients with CLD. According to Beyoglu et al (cited herein), "Whether provoked by obesity and diabetes, alcohol use or oncogenic viruses, the liver develops a core metabolomic phenotype (CMP) that involves dysregulation of bile acid and phospholipid homeostasis. The CMP commences at the transition between the healthy liver (Phase 0) and NAFLD/NASH, ALD or viral hepatitis (Phase 1). This CMP is maintained in the presence or absence of cirrhosis (Phase 2) and whether or not either HCC or CCA (Phase 3) develops. Inflammatory signaling in the liver triggers the appearance of the CMP. Many other metabolomic markers distinguish between Phases 0, 1, 2 and 3. A metabolic remodeling in HCC has been described but metabolomic data from all four Phases demonstrate that the Warburg shift from mitochondrial respiration to cytosolic glycolysis foreshadows HCC and may occur as early as Phase 1. The metabolic remodeling also involves an upregulation of fatty acid β-oxidation, also beginning in Phase 1. The storage of triglycerides in fatty liver provides high energy-yielding substrates for Phases 2 and 3 of liver pathology."

A comprehensive review of metabolomics studies show that all forms of CLD similarly present the following CMP-associated changes:
extreme oxidative stress,
increased β-oxidation of fatty acids,
a shift from aerobic respiration to anaerobic glycolysis,
increased glutathione/cysteine/thiol cycling,
dysregulation of phospholipid and bile acid homeostasis and
increased storage of cytosolic fatty acids and triacylglycerides in fatty liver.

Most of these CMP-associated metabolic alterations involve up-regulated biosynthetic pathways whose end-products experience greater utilization and consumption. CLD-induced up-regulated biosynthetic pathways experience greater flux of metabolites, while the biosynthetic end-products of these pathways experience decreased availability or depletion due to greater utilization. Increased cycling of CMP-upregulated metabolites, therefore, is regarded as increased metabolic demand associated with CLD.

In other words, CLD causes alterations to the phenotype of the host by altering and up-regulating specific metabolic/ biosynthetic pathways. The combined metabolic alterations induced by CLD create increased metabolic demand and utilization for CMP-upregulated metabolites and nutrients. Increased metabolic demand translates into increased nutritional requirements for these metabolites. Therefore, increased metabolic demands associated with CMP-upregulated metabolites define the new distinctive nutritional requirements of CLD patients.

Identification of these CLD-altered metabolic/biosynthetic pathways is necessary to develop a science-based medical food. The term medical food, as defined in section 5(b) of the Orphan Drug Act (21 U.S.C. 360ee (b) (3)) is "a food which is formulated to be consumed or administered enterally under the supervision of a physician and which is intended for the specific dietary management of a disease or condition for which distinctive nutritional requirements, based on recognized scientific principles, are established by medical evaluation."

Therefore, what is needed is a medical food for CLD patients that supplies appropriate amounts of specific nutrients for which CLD patients experience greater demand and utilization. This medical food for CLD patients will support their new distinctive nutritional requirements.

SUMMARY

The subject matter of this application may involve, in some cases, interrelated products, alternative solutions to a particular problem, and/or a plurality of different uses of a single system or article.

In one aspect, an ingestible composition is provided. The composition may comprise N-Acetyl Cysteine in a range of 500-5,000 mg; Polyenylphosphatidylcholine in a range of 500-10,000 mg; and Alpha Lipoic Acid in a range of 200-2,500 mg. This composition may be divided into individual serving sizes for administration. In a further aspect, the composition may further comprise at least one of L-Lysine; L-Arginine; Vitamin C; N-Acetyl L-Carnitine; Betaine HCl; L-Glutamate; Turmeric; Proanthocyanidins; *Nigella sativa*; Pantothenic acid; Benfotiamine; Magnesium; Vitamin E; *Cynara scolymus*; L-Glycine; Vitamin B1; Vitamin B2; Ubiquinol; *Piper cubeba; Artemisia absinthium*; Vitamin B3; Vitamin B6; Zinc; Vitamin D3; Folate; Vitamin B12; Selenium; and Biotin.

In another aspect, medical food composition selected to aid in a reversal of liver fibrosis is provided. The composition may comprise N-Acetyl Cysteine in a range of 500-5,000 mg; Polyenylphosphatidylcholine in a range of 500-10,000 mg; and Alpha Lipoic Acid in a range of 200-2,500 mg. This composition may be divided into individual serving sizes for administration. In a further aspect, the composition may further comprise at least one of L-Lysine; L-Arginine; Vitamin C; N-Acetyl L-Carnitine; Betaine HCl; L-Glutamate; Turmeric; Proanthocyanidins; *Nigella sativa*; Pantothenic acid; Benfotiamine; Magnesium; Vitamin E; *Cynara scolymus*; L-Glycine; Vitamin B1; Vitamin B2; Ubiquinol; *Piper cubeba; Artemisia absinthium*; Vitamin B3; Vitamin B6; Zinc; Vitamin D3; Folate; Vitamin B12; Selenium; and Biotin.

BRIEF DESCRIPTION OF THE FIGURE

FIG. 1 provides a flow chart of an embodiment of use of the medical food of the present invention.

DETAILED DESCRIPTION

The present medical food composition accomplishes the need of providing CLD patients with their new distinctive nutritional requirements. The present invention is a new medical food intended to fulfill the specific dietary requirements of patients with CLD for which distinctive nutritional requirements, based on established epigenetic, metabolomic and other types of scientific research, are established.

The composition of the present invention is referred to herein as a "medical food" or the "medical food of the present invention." This term is intended to apply to the composition discussed for the treatment contemplated. However, it should be understood that the composition of the present invention may be used as a dietary supplement formula, as well as a drug (such as an FDA approved drug) formula.

The complex list of metabolites that are required to stabilize these interlinked up-regulated metabolic pathways can only be provided by a strategic and comprehensive medical food. The complex balance between the medical food's numerous nutrients and The medical food's requirement of continuous administration three times per day could not be reasonably provided by simple alterations of diet alone.

In a particular embodiment, the medical food may be administered orally in divided doses of eight capsules taken three times a day (morning, afternoon, and evening) for a total of twenty four capsules daily. However, it should be understood that the formulation may also be supplied as a liquid drink, tablet, powder, gel, emulsion, micelles, liposomes, and the like.

Further, CLD is not a nutrient deficiency disease like scurvy or pellagra, in which the supplementation of a particular deficient nutrient or dietary supplement may correct symptoms caused by deficiencies of a person's normal nutritional requirements. Similarly, ALD does not simply alter the metabolism of the patient while he is drinking. Rather the abuse of alcohol may change the patient's metabolism in the long-term and alter his nutritional requirements in ways that require fulfillment even after the patient has quit drinking. The medical food is designed to address and correct the results of unfulfilled nutritional requirements in CLD patients.

The medical food satisfies the new distinctive nutritional requirements of CLD patients with a comprehensive list of required metabolites designed to fortify and balance all CMP interlinked and upregulated metabolic pathways associated with patients with CLD. Research shows that these linked CMP-upregulated biosynthetic pathways experience concurrent increased demand and utilization. Therefore, a comprehensive and balanced approach is necessary in order to fulfill the new distinctive nutritional requirements of CLD patients.

Each medical food daily dose is split into three separate administrations in order to satisfy the constant increased nutritional requirements of CLD patients. The medical food's 3× daily administration is designed to achieve optimal periods of homeostasis in CMP-disrupted systems for as long as possible throughout the day. Once or twice daily administrations of medical food will not be as effective as the present invention's three-time-daily administration, even with the same total daily amount. This is because the medical food of the present invention is designed to provide increased nutrient delivery to the cells of CLD patients in an optimal manner throughout the day, and a three-time-daily administration is necessary to achieve this purpose.

The medical food has identified all known metabolic pathways demonstrating CMP up-regulation in CLD. Fulfilling the new distinctive nutritional requirements for CLD patients is accomplished by supplying the necessary balanced amounts of critical nutrients and metabolites for increased flux into CMP-associated up-regulated pathways.

The present invention is a medical food that fulfills new distinctive nutrient requirements for patients with CLD. Medical foods are not drugs and by regulation may contain only GRAS (Generally Recognized As Safe) ingredients. Every ingredient in the medical food is classified as GRAS by the FDA. Further, each ingredient in the medical food formula is in proper balance and proportion for safe administration. The medical food GRAS ingredients are required to provide nutritionally balanced support for CMP up-regulated metabolic/biosynthetic/antioxidant pathways and homeostatic activity in CLD patients.

The medical food is not intended to treat or cure CLD. Rather, the medical food for chronic liver disease of the present invention is intended to satisfy the new distinctive nutritional requirements of CLD patients. Our intention is for the present invention's status as a medical food to be satisfied by even the FDA's narrowest interpretation of the statute. In the present clinical setting, there is evidence of a need for such a science-based medical food for CLD patients.

Core Metabolic Phenotype Comprehensively Identifies CLD-Altered Metabolic/Biosynthetic Pathways As shown below, all CLD exhibit very similar changes to core metabolic phenotype (CMP), regardless of CLD etiology. Specific studies will demonstrate that the same list of CMP-associated metabolic alterations occur in each and every type of CLD. The purpose of this exercise is to establish that due to the very similar nature of these CLD-induced metabolic disruptions, all patients with CLD experience the same disrupted metabolic pathways. These disrupted metabolic pathways define the new distinctive nutritional requirements for patients with CLD. It is therefore appropriate to fulfill the new distinctive nutritional requirements of CLD patients by providing the same medical food formula, because the medical food of the present invention addresses the same disrupted metabolic pathways present in every form of CLD, regardless of the etiology. The medical food accomplishes this by providing a balanced and comprehensive medical food formula with scientific justification and up-coming human clinical trials.

CMP is associated with the following global changes in the metabolome of CLD patients:
  Dis-regulation of phospholipid metabolism, as well as cholesterol and bile acid homeostasis,
  Increased storage of cytosolic triglycerides and fatty acids accompanied with altered β-oxidation of fatty acids,
  A shift from aerobic respiration to anaerobic glycolysis,
  Increased utilization of thiol-containing metabolites including increased glutathione/cysteine cycling, CMP-associated metabolic changes listed above combine to create extreme oxidative stress, which the evidence has been well documented in all CLD. Therefore, as stated above, the rest of Part A will be dedicated to establishing the new CMP-associated distinctive nutritional requirements of CLD patients.

The discussion about how to fulfill the new distinctive nutritional requirements of CLD patients will take place in Part B, below.

1. CMP is Associated with Disruption of Phospholipid, Cholesterol and Bile Acid Homeostasis Phosphatidylcholine (PC) Homeostasis Many Metabolomic studies have focused on CMP-associated changes in the lipidome of CLD patients. It has long been known that lipid metabolism experiences widespread disruption in patients with CLD and that these metabolic changes are associated with distinct changes in specific metabolic biomarkers. Of particular interest to metabolomic researchers has been CMP-associated disruption of PC homeostasis. It has been demonstrated in a variety of studies that all types of CLD patients experience decreased PC availability due to increased utilization and/or impaired synthesis in patients with CLD.

For example, a meta-analysis that examined a large body of metabolomic hepatobiliary studies involving patients with all types of CLD documented that lysophosphatidylcholine species (LPCs) were universally depressed while bile acids were found elevated in all forms of CLD. Thus, the study concluded that "It would appear that depressed LPCs and elevated bile acids in serum represent a phenotype of hepatitis and cirrhosis independent of etiological origin . . . .

Cholesterol and Bile Acid Homeostasis

Similarly, CLD-associated CMP changes cause elevated levels of cholesterol and bile acids. Increased cholesterol infiltration of the mitochondrial membrane has been associated with mitochondrial GSH depletion. Bile acids are created from cholesterol and bile acids are found elevated in patients with CLD.

Glycochenodeoxycholic acid (GCDCA) is the main toxic component of bile acid and elevated GCDCA has been shown to be significantly associated with decreased mitofusin 2 (Mfn2) gene expression. Decreased Mfn2 is associated with many mitochondrial-related diseases. This was demonstrated in a study conducted by Chen et al in which normal human hepatocytes induced by GCDCA showed significant decreased in Mfn2 activity resulting in mitochondrial damage. However, this mitochondrial damage was reversed in the lab by stimulating overexpression of Mfn2.

1a. Non-Alcoholic Fatty Liver Disease (NAFLD)—Disruption of PC, Cholesterol and Bile Acid Homeostasis PC Homeostasis NAFLD exhibits CMP-associated disruption of PC biosynthetic pathways. A study comparing human steatotic livers versus non-steatotic livers showed elevated PC metabolites in steatotic livers, indicating increased activity in the PC biosynthetic pathway. Another research study documented rodents who were fed diets that induced fatty liver experienced up-regulated utilization of PC, choline, betaine, and trimethylamine N-oxide. Other human and animal studies have shown PC disruption in NAFLD.

Increased catabolism of PC and phosphatidylethanolamine (PE) species in the liver by phospholipases A1 and A2 release free fatty acids that require β-oxidation in the mitochondria. If these hepatic fatty acids are not adequately oxidized by β-oxidation, then the unused fatty acids will be repackaged in the liver as hepatic triacylglycerols, creating hepatic steatosis (NAFLD) and setting the stage for NASH.

Metabolomic studies show that CMP-associated disruption of PC homeostasis and elevated triacylglycerol production are not simply an intracellular accumulation of fat in the liver but rather a large-scale translocation of lipid stores. Decreased PC availability and increased PC utilization may contribute to increased cholesterol and fatty acid infiltration into cellular and mitochondrial membranes, which may in turn affect mitochondrial glutathione (GSH) transport.

Cholesterol and Bile Acid Homeostasis

In human and animal studies NAFLD causes an increase in lipid species in the liver and serum/plasma, including cholesterol esters and various bile salts. However, NAFLD is marked by less hepatic inflammation, and therefore less bile acids disruption than NASH.

1b. Non-Alcoholic Steatohepatitis (NASH)—PC, Cholesterol and Bile Acid Homeostasis PC Homeostasis NASH is defined as advanced-stage NAFLD accompanied by high inflammatory activity. As much as 67%-80% of NAFLD patients may remain as benign fatty liver with minimal progression to cirrhosis and normal mortality rates compared to the general population. However, approximately 20%-33% of NAFLD patients may progress to NASH.

In both NASH and in NAFLD, triacylglycerols and several fatty acids are shown to be elevated in the liver, while various other fatty acids and lysophosphatidylcholine (LPC) show decreased levels in plasma. Metabolic studies of NAFLD and NASH showed global changes to lipid profiles in both diseases with only a few differences between them—a comparative analysis showed only three phospholipid species with significant changes in serum concentrations in NASH compared with NAFLD. A recent study noted decreased levels of LPC and increased bile acids associated with NASH were not demonstrated in mere steatosis (NAFLD). Differences between NAFLD and NASH appear to be due to the inflammatory component of NASH; this inflammatory component is absent in fatty liver (NAFLD).

A similar study found that Lysophosphatidylcholine acyltransferases (LPCAT), which convert LPC to PC were up-regulated in NASH with a 200%-400% increase in hepatic LPCAT1, LPCAT2, and LPCAT3 mRNAs. A mechanism proposed by Gonzalez et al suggested that hepatic inflammation causing activation of TNFα and TGFb1 in turn cause increased hepatic LPCAT activity resulting in lower serum LPC levels.

Cholesterol and Bile Acid Homeostasis

As noted above, the inflammatory component of NASH may be linked to fatty acids transported to the liver from visceral adipose. NASH-associated inflammation is also linked to bile acid disruption in the liver. Gonzalez et al suggested " . . . the decline in serum LPC and rise in serum bile acids are a signature of the inflammatory component of NASH, rather than the steatotic component." Furthermore, they suggested that hepatic inflammation involving TNFα and TGFb1 activation in the liver causes disruption to bile acids, documenting that the enzymes that uptake the bile salts into the hepatocytes were highly down-regulated, and the transporters that export bile acids from the liver were highly up-regulated in NASH.

1c. Alcoholic Liver Disease (ALD)—PC, Cholesterol and Bile Acid Homeostasis

PC Homeostasis

ALD has long been implicated in disrupted PC metabolism. A study on cirrhotic patients reported that whether cirrhosis was due to alcohol or HBV, there was a decrease in serum LPC of cirrhotic patients compared to healthy volunteers. Animal studies have shown that alcohol exposure may produce pathologies that correlate with NASH. A study on alcoholic micropigs initially showed increased hepatic triglycerides, and then after six months demonstrated inflammation, steatosis and fibrosis. The authors concluded that increased lipid synthesis and reduced LPC synthesis and export were responsible for the accumulation of hepatic triglycerides in ALD. In another study on athymic nude mice gavaged with 5% to 40% ethanol solutions, the findings showed the mice developed a mild hepatic hemorrhage and serum PC was elevated. There was a decrease in saturated and monounsaturated LPC, but polyunsaturated LPC was elevated.

Cholesterol and Bile Acid Homeostasis

Metabolomic ALD studies show that ALD-induced cirrhosis is associated with higher bile acids and lower LPCs (92,94) in a manner almost identical with non-alcoholic and HBV-induced cirrhosis.

1d. HBV and HCV—PC, Cholesterol and Bile Acid Homeostasis

PC Homeostasis

PC biosynthesis is known to be disrupted in both HCV and HBV. A Metabolomic study in China studied HBV patients with deteriorating liver function demonstrated disrupted PC levels. The study describes decreased PC species combined with an elevation of toxic bile acids, glycochenodeoxycholic acid (GCDCA). Another Chinese study reported similar results when examining the progression of chronic HBV to cirrhosis. The same phenomena are also seen in NALFD/NASH, cirrhosis and HCC. An animal study indicated that HCV alters many pathways in the liver with significant changes in LPCs and bile acids, as well as carnitine esters, fatty acids, and LPEs.

A study conducted by Metabolon Inc., in association with the University College Dublin showed the global effects on the hepatic metabolome of HCV infection. Comparative analysis of 250 metabolites of normal hepatocytes was compared to the same panel of metabolites from HCV-infected hepatocytes. The study demonstrated specific changes in metabolism in HCV-infected hepatocytes at 24, 48 and 72 hours, disrupting many different metabolic pathways as a result of HCV infection, most notably fatty acid, phospholipid, GSH, amino acid, nucleotide and methylthioadenosine metabolism. The study showed altered flux through both PC biosynthetic pathways (PEMT and CDP-choline), as well as alteration to all the other CMP-associated pathways.

Cholesterol and Bile Acid Homeostasis

HCV disrupts many aspects of lipid metabolism. Lipids are necessary for HCV viral assembly and secretion. HCV replication modulates host cell lipid metabolism dramatically to enhance its replication. The HCV life cycle requires numerous lipids, which have been shown to be essential modulators of the HCV viral lifecycle.

HCV disrupts cholesterol metabolism by causing proteolytic cleavage of sterol regulatory element binding proteins (SREBPs), thereby inducing steatosis. Bile acids are derived from cholesterol and HCV disrupts bile acid metabolism as well as cholesterol metabolism.

Apolipoprotein and VLDL synthesis is altered in HCV and HCV-infected hepatocytes showed increased production of cholesterol and sphingolipids, both of which HCV utilizes to aid in virion maturation and infectivity. Cholesterol-depleted or sphingomyelin-hydrolysed virus had a negative impact on infectivity. Metabolomic analysis of HCV-infected hepatocytes showed a significant increase in cholesterol and various sphingoid bases.

An animal study was performed in HCV-infected tree shrews, which showed increased bile acids and decreased PC availability; both are hallmarks of CLD-induced CPM alterations. Further, it has been established that HBV, HCV, and NASH all trigger similar metabolomics alterations involving hepatic inflammation-mediated changes to bile acid metabolism. Serum bile acids have been found to be higher in patients with severe fibrosis as compared to patients with moderate fibrosis.

A Metabolomic study on HCV-infected human hepatocytes showed that HCV impaired VLDL production and secretion, which in turn may add to the accumulation of hepatic triglycerides due to decreased VLDL packaging of triglycerides for hepatic export.

A recent HBV metabolomic study noted a decline in serum PC species and also elevated GCDCA levels, one of the main toxic components of bile acids, in HBV-infected patients. Serum bile acids have also been found to be elevated in HCV patients. As mentioned previously, Mitofusin2 (Mfn2) gene expression regulates mitochondrial morphology and signaling. A recent study showed that one of the signature toxic components of bile acids, GCDCA, decreases the expression of Mfn2. Further, stimulation in the lab of overexpression of Mfn2 " . . . effectively attenuated mitochondrial fragmentation and reversed the mitochondrial damage observed in GCDCA-treated . . . " hepatocytes.

This line of research demonstrates how disruption of PC metabolism affects other CMP-associated pathways in various ways—increased SAMe flux into the up-regulated PC pathway in the liver has a negative effect on flux of SAMe into the GSH pathway. Decreased GSH contributes to the disruption of redox homeostasis and the creation of extreme oxidative stress in patients with CLD. In a vicious circle, extreme oxidative stress then further oxidizes existing GSH stores, causing increased GSH cycling. Similarly, decreased PC affects choline metabolism, which in turn controls cholesterol metabolism and bile acid homeostasis. An increase in bile acids creates an increase in GDCDA from toxic bile acids. As mentioned above, GDCDA exacerbates extreme oxidative stress by negatively affecting Mfn2 gene expression. Therefore, disruption of PC availability affects the GSH pathway, and all linked up-regulated CMP pathways contribute to extreme oxidative stress, which is the hallmark of CLD.

2. CMP is Associated with Increased Storage of Cytosolic Triacylglycerides (TGL) in Fatty Liver and Altered β-oxidation of Fatty Acids (FA)

2a. Non-Alcoholic Fatty Liver Disease (NAFLD)—Triacylglycerides (TGL) and Fatty Acids (FA) Accumulation in the Liver Visceral adipose supplies fatty acids to the liver for β-oxidation. PC catabolism is also considered a source of fatty acids for hepatic β-oxidation. Studies indicate that increased levels of hepatic triacylglycerols are also seen in CMP-associated CLD and that those triacylglycerols may be exported from adipose tissue.

Studies have also indicated that visceral adipose, known for being highly inflammatory, may be responsible for exporting the inflammatory component which distinguishes NAFLD from the inflammatory state of NASH.

In fact, both visceral adipose and up-regulated PC metabolism are considered sources of hepatic fatty acids associated with increased hepatic triacylglycerols. Increased catabolism of PC by phospholipases A1 and A2 in the liver release free fatty acids. These free fatty acids require β-oxidation in the mitochondria of hepatocytes. Un-oxidized fatty acids are repackaged as hepatic triacylglycerols, creating NAFLD and setting the stage for NASH.

As noted in section 1b, NAFLD is considered to be the physical manifestation of metabolic syndrome in the liver. Metabolomic studies have found increased lipid species triacylglycerides and diacylglcerides in both liver and blood samples of NAFLD patients.

2b. Non-Alcoholic Steatohepatitis (NASH)—Triacylglycerides (TGL) and Fatty Acids (FA) Accumulation in the Liver NAFLD and NASH are both characterized by changes in the cellular lipid profile. NASH is NAFLD with a major inflammatory component. For years researchers have been searching for the cause of NASH-associated hepatic inflammation, and new studies theorize that adipose tissue, which is intrinsically pro-inflammatory, may be the origin of hepatic inflammation. As mentioned previously, Lipidomic studies show similar significant lipid metabolic disruption in both NASH and NAFLD with only small differences in three PC species to distinguish the two. In NASH as well as NAFLD, triacylglycerols and several fatty acids were shown to be elevated in plasma, while various other fatty acids showed decreased levels in plasma. Other studies also showed that NASH patients with cirrhosis show reduced cellular carnitine levels, which may negatively affect β-oxidation of fatty acids in the mitochondria.

2c. Alcoholic Liver Disease (ALD)—Triacylglycerides (TGL) and Fatty Acids (FA) Accumulation in the Liver Early on, Leiber found a correlation with ethanol intake and the accumulation of hepatic fatty acids and triglycerides. Leiber also showed that ethanol has extreme effects on lipid peroxidation. Metabolomic studies suggest that hepatic fatty acids and triacylglycerides increase and plasma fatty acids and PC species decrease in ALD.

2d. HBV and HCV—Triacylglycerides (TGL) and Fatty Acids (FA) Accumulation in the Liver In Section 1 we showed that CLD-associated CMP exhibits up-regulated cholesterol utilization, which supplies the liver with fatty acids from PC catabolism. These PC-derived hepatic fatty acids require β-oxidation or they will be re-packaged as hepatic triacylglycerols, contributing to fatty liver. We have shown in Section 1d above that both HCV and HBV infections affect PC metabolism and increase hepatic fatty acids and triacylglycerides.

We also discussed that visceral adipose is also a source for both hepatic fatty acids and hepatic triacylglycerols. The HCV-infected tree shrew study (*Tupaia belangeri chinensis*) suggested that HCV causes alterations in carnitine esters and fatty acids.

HCV patients have been shown to have low levels of carnitine species, which impairs β-oxidation of fatty acids. An extensive metabolomics study on HCV-infected hepatocytes showed that HCV infection causes an increase in lipid content within hepatocytes, or liver steatosis. Steatosis is the accumulation of intracellular fatty acids in the liver, and it has been associated with HCV infection, increased oxidative stress and progression to liver cirrhosis. HCV causes proteolytic cleavage of sterol regulatory element binding proteins (SREBPs), thereby increasing cholesterol and inducing steatosis.

Further, fatty acid oxidation is disrupted during HCV infection and it is associated with HCV-induced metabolic L-Carnitine deficiency. A metabolomic analysis of HCV-infected hepatocytes showed that HCV disrupts fatty acid β-oxidation and fatty acid transport to the mitochondria. The study also showed that HCV-infected hepatocytes have an increase in fatty acid concentration and a decrease in mediators of fatty acid transport Acyl-carnitine (necessary for fatty acid transport to the mitochondria from the cytosol) and proper mitochondrial function have been shown to be depleted in HCV. Further, the metabolomic study showed a significant decrease in coenzyme A (CoA), pantothenic acid, acetylcarnitine and a number of carnitine derivatives at 48 and 72 hours post-infection, indicating that fatty acid transport to the mitochondria may also be disrupted.

3. CMP is Associated with a Shift from Aerobic Respiration to Anaerobic Glycolysis (Warburg Shift)

In the Introduction, we described the new distinctive CMP as it progresses through the different phases of CLD. One of the CMP-associated changes we noted was the "Warburg shift", which involves a shift in metabolism from aerobic respiration to anaerobic glycolysis. This shift to anaerobic glycolysis has usually been associated with HCC, but recent metabolomic studies have shown that the shift happens early in all CLD.

As stated previously, the shift from aerobic oxidative phosphorylation to cytosolic anaerobic glycolysis is a hallmark of CLD-associated CMP. The Warburg shift is associated with alterations of metabolic pathways that are linked to both cell proliferation and nutrient acquisition, while the shift to anaerobic glycolysis comes at the expense of ATP production.

3a, 3b. NAFLD and NASH—Warburg Shift

Insulin resistance is associated with NAFLD/NASH. In mice, insulin is reported to activate pyruvate kinase M2, which is the enzyme that triggers cytosolic glycolysis involved in the Warburg shift. The shift from aerobic respiration to anaerobic glycolysis results in the production of lactate and alanine from pyruvate. The Warburg shift occurs as early as Phase 1 in NAFLD/NASH progression.

3c. ALD—Warburg Shift

ALD progresses towards a shift in aerobic respiration to anaerobic glycolysis along the parallel path of fibrosis/cirrhosis, CMP expression and HCC development 3d. HBV and HCV—Warburg Shift Metabolomic studies have documented the Warburg shift occurs in all types of CLD, including HBV and HCV as early as phase one, long before the appearance of HCC.

Furthermore, HCV has been found to shift metabolism from aerobic respiration towards the pentose phosphate pathway. The pentose phosphate pathway is a parallel pathway with anaerobic glycolysis. In other words, the pentose phosphate pathway creates NADPH and five-carbon sugars, which are then oxidized by glycolysis in HCV patients.

4. CMP is Associated with GSH Depletion, Increased Consumption of Thiol-Containing Metabolites, Extreme Oxidative Stress and Altered One-Carbon Metabolism CLD of all etiologies are associated with CMP-induced hepatic extreme oxidative stress. Glutathione is the master controller of cellular redox status, maintaining and regulating the redox status of cellular enzymatic and non-enzymatic (small-molecule) antioxidants. CLD-associated depletion of GSH may cause depletion of all linked cellular antioxidants that are normally maintained and regulated by GSH.

4a, 4b. NAFLD and NASH—altered Homocysteine/Glutathione/One-Carbon Metabolism

Metabolomic analyses on a variety of types of NAFLD samples have been performed on animal models, living human subjects and human tissue samples. One common finding is that cysteine-glutathione disulfide and both oxidized and reduced glutathione were depressed in the liver and serum/plasma, and this condition is associated with extreme oxidative stress in patients with NAFLD/NASH.

The progression of steatosis (NAFLD) to steatohepatitis (NASH) involves the sensitization of hepatocytes through oxidative stress to cytokine-induced apoptosis and the importation of inflammatory fatty acids from adipose tissue. Depletion of mitochondrial glutathione (mGSH) is associated with cholesterol infiltration of mitochondrial membranes, which lowers transmembrane potential, and which in turn inhibits the transport of cytosolic GSH into the mitochondrial membrane. Glutathione depletion has been found to be involved with hepatic stellate cell activation.

One of the most common research models for inducing steatosis is the methionine and choline deficient diet (MCD). MCD is associated with steatosis, mitochondrial dysfunction, hepatocellular injury, oxidative stress, inflammation, and fibrosis. One study analyzed the contributions of both the methionine deficient diet (MD) and the choline deficient diet (CD) to total MCD pathogenic effect. They found that MD reproduced most of the deleterious effects of the total MCD, while CD caused mainly steatosis, with a rise in hepatic FA and TGL accumulations, but without much of the other deleterious effects associated with MCD.

The study found that S-adenosylmethionine (SAMe) and glutathione (GSH) depletion in the mitochondria precede the observed effects due to decreased mitochondrial membrane fluidity associated with a lower phosphatidylcholine/phosphatidylethanolamine ratio.

GSH or SAMe therapy restored GSH in the mitochondria and ameliorated hepatocellular injury in mice fed either a MCD or MD diet.

4c. ALD—Altered Homocysteine/Glutathione/One-Carbon Metabolism

Alcohol toxicity has also long been linked to folate/homocysteine or one-carbon metabolism disruption. Early research established significant ethanol-associated glutathione depletion and oxidative stress, altered methionine metabolism, altered folate/homocysteine/one-carbon metabolism, malnutrition, and increased Kupffer cell activation. Alcohol induced oxidative stress and inflammation has been shown to exacerbate the progression of the disease.

Changes in gene expression can be accomplished through alterations in DNA coding sequence. Changes in gene expression and phenotype may also be caused by other mechanisms. Epigenetics is the study of these heritable changes. DNA can be modified epigenetically by DNA methylation, histone modifications, and RNA-based mechanisms. Recent studies have focused on epigenetic features, transcriptional factors and signaling pathways associated with chronic ALD. These new studies provide greater nuanced perspectives of ALD/CLD disease pathology. Consumption of ethanol causes epigenetic changes (CMP) that contribute to ALD. In an extensive study, ethanol affected metabolism of methionine and thereby DNA methylation. ALD is associated with GSH depletion in the mitochondria. Studies show that ALD-induced mitochondrial GSH depletion is associated with cholesterol-enrichment of the mitochondrial membrane, which leads to impairment of GSH transport of cytosolic GSH into the mitochondria in both ALD and NAFLD/NASH.

4d. HBV and HCV—Altered Homocysteine/Glutathione/One-Carbon metabolism

Both HCV and HBV induce hepatic oxidative stress. The mechanisms for increasing oxidative stress in both pathologies are well known. These mechanisms involve epigenetic changes caused by viral proteins interacting with both mitochondria and endoplasmic reticulum (ER) to increase mitochondrial reactive oxygen species (ROS) generation. HCV core expression inhibits electron transport at Complex I, and increase Complex I ROS production. They also induce depletion of mitochondrial GSH, increase mitochondrial membrane permeability and impair various antioxidant defense mechanisms.

A metabolomic study on HCV-infected hepatocytes showed changes to the GSH pathway at 24, 48 and 72 hours, demonstrating that HCV caused six or seven specific epigenetic changes to the metabolome. These findings are consistent if not identical with the phenotypic expression of the CMP seen in all forms of CLD.

HCV-mediated mitochondrial disruption is a causative factor in GSH depletion and the creation of extreme oxidative stress. HCV has been shown to create replication sites in the mitochondrial membrane that damages mitochondrial form and function. HCV has also been shown to disrupt the GSH metabolic pathway, causing greater utilization of GSH and disrupted biosynthesis. HCV-impaired GSH biosynthesis contributes to a large increase in ROS generation that further contributes to mitochondrial GSH depletion.

5. CLD/CMP-Associated Extreme Oxidative Stress and Fibrogenesis

CLD causes extreme oxidative stress as a result of CMP-associated metabolic disruptions and unfulfilled distinctive nutritional requirements. NASH, ALD and HBV all have been associated with extreme oxidative stress. CLD-induced metabolic changes increase ROS and NOS levels, which disrupt redox homeostasis and create extreme oxidative stress. Depletion of GSH results in the inability to counteract oxidative-mediated insults to cellular systems, resulting in irreversible cellular degeneration and cell death. GSH depletion and CLD-associated oxidative stress may damage mitochondria form and function. Furthermore, non-enzymatic small molecule antioxidants and antioxidant minerals are both depleted as a result of CLD-induced oxidative stress, GSH depletion and cirrhosis.

GSH is the main regulator of cellular redox homeostasis and redox signal transduction. Under normal metabolism, cellular redox status is maintained and regulated by the glutathione redox couple GSH:GSSG (GSSG is an oxidized form of GSH), along with the NADPH/NADP+ and Trx-SH/Trx-SS redox couples. Redox balance is involved in cellular signal transduction, and small changes in the GSH:GSSG ratio are involved in the fine-tuning of signal transduction in physiological events such as cell cycle regulation and other processes.

The interaction of GSH and the free-thiol in cysteine residues forms a mixed disulfide that is reversibly formed through protein-S-glutathionylation to protect proteins from irreversible oxidative stress. Protein-S-glutathionylation is an important mechanism for post-translational regulation of a large list of regulatory, structural and metabolic proteins that play roles in cell signaling and metabolic pathways. Protein-S-glutathionylation production requires a reactive cysteinyl residue, present at physiological pH in the thiolate form. Under oxidative stress, these cysteinyl residues may be oxidized and react with GSH leading to a glutathionylated-cysteine derivative. Both GSSG and S-glutathionylated proteins may be catalytically reduced back to GSH, while they both may also be reduced back to GSH non-enzymatically.

Protein-S-glutathionylation is an important mechanism for post-translational regulation. Regulatory, structural and metabolic proteins that react with GSH to form S-glutathionylated proteins are involved in cell signaling and the regulation of cellular metabolic pathways.

Disruption of GSH-controlled cellular redox homeostasis increases oxidative stress. Disruption of GSH homeostasis has been implicated in the pathogenesis and progression of many human diseases. Decreased GSH levels contributing to oxidative stress have been associated with aging, neurodegeneration, inflammation, and infections.

Besides countering ROS-associated oxidative stress, GSH is also critically involved in mediating the susceptibility of nitric oxide (NO) and NO derivatives in the body. GSH is involved in countering Reactive Nitrogen Species (RNS) associated oxidative stress and counteracting RNS-mediated damage. CLD increases ROS and NO levels, which disrupt redox homeostasis and create extreme oxidative stress. As mentioned above, depletion of GSH results in the inability to counteract oxidative stress and NO-mediated insults to hepatic cellular systems, resulting in irreversible cellular degeneration and cell death.

Extreme hepatic oxidative stress and oxidative stress-mediated hepatic inflammation trigger the separate process of liver fibrogenesis. Hepatic fibrogenesis involves a process whereby CMP-associated oxidative stress triggers the conversion of normally quiescent hepatic stellate cells into active collagen-secreting myofibroblasts.

Part B: The medical Food Contemplated Herein Fulfills the New Distinctive Nutritional Requirements for Patients with CLD In Part A we established that all forms of CLD create distinctive epigenetic changes in the phenotype and alterations of metabolism in patients with CLD. We also established that these changes are similar, and in most cases identical in all forms of CLD, regardless of the disease etiology. Extensive metabolomic studies on all forms of hepatobiliary diseases have collectively labeled these new distinctive metabolic/phenotypic changes as the new Core Metabolic Phenotype (CMP) for CLD patients.

As noted previously, these CMP phenotypic changes are very similar in all CLD, whether they involve epigenetic changes and/or metabolic alterations associated with chronic ALD, NAFLD, NASH or oncogenic viruses like HCV or HBV. These CMP-associated changes result in the up-regulation of specific biosynthetic metabolic pathways, which increases the metabolic demand for metabolites and end-products involved in those biosynthetic pathways.

A person's complete nutritional requirements are defined as the sum of a person's combined metabolic demands. Therefore the new distinctive nutritional requirements of CLD patients must factor in increased demand for metabolites and end-products of up-regulated biosynthetic pathways associated with CLD.

A medical food for CLD patients must strategically identify, coordinate and supply the proper amount and balance of metabolites necessary to fulfill the new distinctive nutritional requirements of CLD patients. Disrupted CMP-associated metabolic pathways are listed below:

Dis-regulation of phospholipid metabolism and membrane phospholipid reallocation,
Dis-regulation of cholesterol and bile acid homeostasis,
Increased storage of cytosolic triglycerides and fatty acids accompanied with altered β-oxidation of fatty acids,
A shift from aerobic respiration to anaerobic glycolysis,
Increased utilization of thiol-containing metabolites including increased glutathione/cysteine cycling, increased SAM/SAH/methionine cycling and increased one-carbon methylation metabolism The CMP-related metabolic alterations listed above involve up-regulation and increased cycling of metabolites involved in the following up-regulated biosynthetic pathways:

The GSH pathway as well as other GSH-linked antioxidant systems, including cellular small molecule non-enzymatic antioxidants and mitochondrial metabolites
Both phosphatidylcholine (PC) biosynthetic pathways (PEMT and CDP-choline) and mitochondrial metabolites associated with mitochondrial membrane form, function and transmembrane potential
The SAM/SAH/methionine cycle with associated one-carbon methylation metabolism
Amino acid metabolism There is ample evidence that depletion of biosynthetic metabolites in one CLD-altered pathway may exacerbate other existing CLD-altered pathways. This is due to the fact that CLD/CMP-altered biosynthetic pathways are interlinked and most of these up-regulated pathways draw directly on SAMe stores. These interlinked pathways include the GSH and PC pathways as well as the SAM/SAH/methionine cycle and one carbon metabolism. Nutritional depletion of key nutrient metabolites in these interlinked metabolic pathways may have a synergistic effect on promotion of extreme oxidative stress, which is the hallmark of CLD.

As noted in Section A, extreme hepatic oxidative stress and oxidative stress-mediated inflammation triggers the process of hepatic fibrogenesis. Fibrogenesis involves the conversion of hepatic stellate cells into myofibroblasts. Myofibroblasts secrete collagen into the extracellular spaces of the liver, resulting in fibrosis and cirrhosis.

While liver fibrosis was once considered irreversible, modern studies have demonstrated that once the trigger to fibrogenesis (extreme oxidative stress) is switched off, myofibroblasts apoptosis may occur while hepatic stellate cells remain quiescent and the process of collagen resorption may then proceed at a fairly constant rate. The process of collagen resorption is well established and has been demonstrated in numerous animal and human CLD studies.

SAMe is the most ready methyl donor of all the one-carbon methylation donors, so it is no surprise that all CMP up-regulated biosynthetic pathways similarly draw on SAMe. SAMe is also involved in the transsulfuration pathway in GSH synthesis. Further, there is a large body of existing current and historical studies involving exactly these same CMP metabolic pathway alterations and the interlinked effects that one altered pathway may have on other CMP pathways. Dr. C. S. Leiber was a pioneer in this area and performed a series of seminal studies on ALD and liver cirrhosis.

CMP alterations establish a vicious positive feedback loop regarding CLD-induced oxidative stress: CMP-altered metabolic pathways create extreme oxidative stress, and extreme oxidative stress negatively affects the altered CMP metabolic pathways. Extreme oxidative stress causes increased oxidation of: PC to oxidized PC; methionine to methionine sulfate; homocysteine to homocystine; cysteine to cystine; GSH to GSSG, GCDCA in bile acid, and proteins to PrS-SC, PrS-SG, and PrS-SCG. These oxidized metabolites require reduction to reactivate their healthy roles in metabolism. Accumulation of oxidized forms of these metabolites may have negative implications for health. For instance, oxidized PC may cause apoptosis in macrophages and affect cell viability ( ).

A recent review of GSH studies concluded that, "Conditions characterized by increased ROS levels may require not only enhanced GSH action to maintain redox status, but also augmented energy supply and precursors to replace/enhance GSH content and/or transport it to the places where it is needed". Further, extreme oxidative stress may decrease SAMe availability, which contributes to DNA hypomethylation and oxidation. DNA hypomethylation may induce and/or exacerbate further alterations to CMP gene expression. Extreme oxidative stress has been identified as a trigger to hepatic stellate cell conversion in the process of hepatic fibrogenesis.

PC supplementation has also been studied in CLD, as has SAMe supplementation. While animal studies have shown promise, human studies targeting individual metabolites have been inadequately controlled and have shown mainly inconclusive results. There have been calls for human clinical trials involving combinations of these CLD up-regulated metabolites.

The medical food clinical trials will demonstrate that its treatment serves to decrease oxidative stress and/or re-establish redox homeostasis in study patients. This in turn will down-regulate fibrogenic activity and slow down or stop the progression of fibrosis while allowing the reversal of fibrosis to occur. This reversal of liver fibrosis is a primary and unexpected advantageous result of the present invention. Reports of reversal of fibrosis in ALD patients who have quit drinking vary and have been inconsistent, while there has been a dearth of studies regarding this topic. Therefore, clinical trials of the present invention will determine if and/or when reversal of fibrosis is possible in non-drinking, compliant patients with ALD. If the initial clinical trial finds that reversal of fibrosis is possible in ALD patients, future studies on non-drinking compliant patients with ALD may be necessary to determine whether reversal of fibrosis may be induced or accelerated by fulfilling the distinct nutritional requirements of patients with ALD and stabilizing their altered metabolic pathways. Meanwhile, past studies have shown reversal of fibrosis after the underlying etiology is eliminated in HCV, HBV, NASH autoimmune hepatitis, and secondary biliary fibrosis. The medical food clinical trials will investigate whether the fibrogenic activity associated with CLD may be down-regulated by fulfilling the distinctive nutritional requirements of CLD patients, and furthermore, whether reversal of fibrosis may be accomplished even in the presence of continuing CLD in the cases of HCV, HBV and NAFLD/NASH patients or in the chronically altered phenotype of non-drinking compliant ALD patients.

The medical food clinical trials will monitor changes in liver fibrosis staging in CLD patients over time. Any positive improvement in fibrosis staging may be due to down-regulation of the fibrogenic activation caused by fulfillment of the distinctive nutritional requirements of the CLD patients. Conversely, any additional progression of fibrosis may be associated with the direct action of CLD rather than unfulfilled nutritional requirements of the CLD patients.

Previous Studies

Over the last several decades Dr. CS Lieber published over 80 studies on ALD, cirrhosis, SAMe and PC. Dr. Leiber was responsible for many important discoveries including the microsomal ethanol oxidizing system (MEOS) involving cytochrome P4502E1. Dr. Leiber performed many important animal studies involving PC and SAMe administration in ALD. Early on, Dr. Leiber noted that PC supplementation decreased oxidative stress, correctly observing that supplying the biosynthetic end-product of the PC biosynthetic pathway decreases draw on SAMe, which is then re-directed to GSH biosynthesis. Dr. Lieber observed that the resulting up-regulation in GSH production was responsible for the observed decrease in oxidative stress.

Dr. Leiber went on to study PC and SAMe administration in rats and baboons fed ethanol, noting that PC administration attenuated CCl4 and ethanol-induced liver injury, while SAMe restored hepatic GSH levels and had a positive effect on mitochondrial lesions and leakage. In 2002, Dr. Leiber pointed to promising animal studies and called for human studies involving administration of SAMe to patients with ALD, noting that " . . . therapeutic administration of SAMe should be the subject of a comprehensive clinical trial to assess its capacity to attenuate early stages of alcoholic liver injury in human beings."

Numerous other studies, for instance, a 1989 Scandinavian human study reached the same conclusions, seeing a "significant increase" in levels of hepatic glutathione, in patients with both alcoholic and non-alcoholic liver diseases—"SAMe may therefore exert an important role in reversing hepatic glutathione depletion in patients with liver disease."

Dr. Leiber pointed out that the immediate metabolic precursor of SAMe is methionine, but methionine must be enzymatically activated to SAMe, and this enzyme is impaired in ALD. Therefore, he warned against administering methionine instead of SAMe due to this enzymatic inhibition, "The precursor of SAMe is methionine, one of the essential amino acids, which is activated by SAMe-synthetase (EC 2.5.1.6). Unfortunately, the activity of this enzyme is significantly decreased as a consequence of liver disease. Because of decreased utilization, methionine accumulates and, simultaneously, there is a decrease in SAMe that acquires the status of an essential nutrient and therefore must be provided exogenously as a super nutrient to compensate for its deficiency."

A 2011 review described various studies regarding the efficacy of treating patients with ALD metabolic disorders with SAMe. The authors conclude that because recent SAMe studies are inconclusive or contradictory, the one-carbon methyl donors associated with homocysteine/methionine conversion should be included in future SAMe ALD studies, "The doors have now been opened for potentially productive research into the relationship of epigenetic changes in SAM-regulated gene methylation to all pathways of liver injury in ALD. Furthermore, the inconclusive results of trials in SAM treatment of ALD suggest that provision of other nutritional factors involved in SAM metabolism, such as vitamin B-6, should be included with SAM in larger and more prolonged clinical trials."

A symposium titled, "Role of S-Adenosyl-L-Methionine (SAMe) in the Treatment of Alcoholic Liver Disease" was sponsored by The National Institute on Alcohol Abuse and Alcoholism and the Office of Dietary Supplements, National Institutes of Health in Bethesda, Md., September 2001, also discussed SAMe with a potential role in ALD:

"The presentations of this symposium support the suggestion that SAMe may have potential to treat ALD by (1) acting as a precursor of antioxidant glutathione, (2) repairing mitochondrial glutathione transport system, (3) attenuating toxic effects of proinflammatory cytokines, and (4) increasing DNA methylation."

Dr. Leiber studied SAMe depletion in early ALD and noted that decreased SAMe levels occur even before SAMe-synthetase is inhibited. Dr. Leiber attributed SAMe depletion to extreme oxidative stress associated with the metabolism of alcohol, which rapidly consumes GSH. Because SAMe is one of the rate-limiting steps in GSH biosynthesis, exogenous SAMe administration was an object of many studies by Dr. Leiber on patients with ALD, and his conclusions all favored human clinical trials involving SAMe and PC administration in patients with CLD.

However, several recent SAMe studies on CLD have shown inconclusive or inconsistent results. One recent study showed that oral SAMe administration has low bioavailability, and the authors recommend esterifying the molecule to form a "more lipid-soluble prodrug". Therefore, low oral SAMe bioavailability may be a significant contributing factor to the inconsistent results seen in various recent SAMe studies. Further, SAMe is contraindicated for patients with bipolar disorders and Parkinson's disease and it is associated with serotonin metabolism, so use of serotonin-related drugs are contraindicated for SAMe use as well.

For the reasons listed above, the present invention does not include SAMe as a required metabolite in its formula. The medical food compensates for this omission in three ways:

First, it has been proposed above that SAMe contributes four major benefits in CLD; further, increased GSH production by SAMe is generally regarded as the most significant benefit. Significantly, there are two rate-limiting metabolites in the GSH biosynthetic pathway: S-adenosylmethionine (SAMe) and N-acetylcysteine (NAC). In other words, administration of either SAMe or NAC will promote GSH production. The medical food of the present invention chooses to fulfill the distinctive metabolic requirements of the CMP-associated up-regulated GSH pathway by providing NAC as the rate-limiting metabolite instead of SAMe to stabilize the GSH pathway and to increase GSH synthesis. NAC safely and effectively increases GSH production without affecting the SAM/SAH/methionine pathway; thereby fulfilling CMP-increased metabolic demand for GSH metabolites while simultaneously saving SAMe for other uses including proper DNA methylation. Importantly, proper GSH bioavailability will work to reduce CMP-associated oxidative stress and CLD metabolic perturbations associated with extreme oxidative stress.

Second, just as Dr. Leiber noted early on, providing PC decreases oxidative stress by reducing the flux of SAMe into the highly up-regulated PC pathways in CLD. Therefore, PC administration resulted in more SAMe availability for GSH production. In the same way, administration of NAC also increases SAMe availability, because NAC administration reduces the draw of SAMe into the GSH pathway. The result of fulfilling the increased metabolic demand for metabolites in both of these up-regulated CMP-associated pathways is that SAMe is less utilized, saving SAMe for other metabolic functions, including DNA methylation.

Third, supplementing the one-carbon metabolite betaine corrects SAMe-synthetase deficiency and effectively restores methionine conversion to SAMe, as Dr. Leiber pointed out that SAMe-synthetase is inhibited in ALD. In fact, administration of one-carbon metabolites has been shown in many CLD studies to restore proper SAM/SAH/methionine cycling, including homocysteine to methionine cycling, and methionine to SAMe cycling. Many researchers have concluded that future glutathione studies must necessarily include one-carbon metabolites as well as metabolites of the SAM/homocysteine cycle.

Most of the nutritional studies to date have focused on single metabolites or single metabolic pathways in various conditions of CLD. However, the interlinked nature of these CMP-altered metabolic pathways beg for a comprehensive and systematic approach to fulfill the distinctive nutritional requirements of CLD patients. For instance, many researchers have stated the need to add the one-carbon methyl donors to any future CLD studies involving SAMe. As noted previously, many researchers have advocated a multi-ingredient approach to future human CLD clinical trials due to the interlinked nature of the CLD affected metabolic pathways. The medical food supplies the one-carbon metabolites, as well as the precursor metabolites and the end-product metabolites to all CLD-affected biosynthetic pathways. The medical food phase II human clinical trials will administer CMP-associated metabolites in a comprehensive and systematic approach to fulfill up-regulated CMP metabolic demand with proper levels of required metabolites. The medical food clinical trials will examine the effects of this regimen using FibroScan, a non-invasive device, to assess liver stiffness, which correlates well with fibrosis staging in patients with CLD.

The medical food does not treat CLD—it will not cure or treat HCV, HBV, NASH or ALD; rather it satisfies the new distinctive nutritional requirements of patients with CLD. Extreme oxidative stress is created in CLD in part as a result of unfulfilled nutritional requirements of patients. Fulfilling the distinctive nutritional requirements of CLD patients may therefore decrease oxidative stress. If long-term re-establishment of redox homeostasis may be achieved, then improvement in fibrosis staging may be possible. This is because fibrogenesis is not a direct action of CLD. Fibrogenesis is a separate hepatic process that is triggered by extreme oxidative stress associated with CLD, but fibrosis is not caused by any direct action of CLD. In fact, GSH depletion and oxidative stress have been implicated in triggering fibrogenesis through hepatic stellate cell conversion to myofibroblasts. Metabolomic studies have implicated CMP-associated metabolic disruptions to the creation of CLD-associated extreme oxidative stress. In other words, CLD-associated extreme oxidative stress is at least in part the result of unfulfilled metabolic requirements of patients with CLD, resulting in decreased availability or depletion of necessary metabolites of the PC, GSH, SAMe, and one-carbon metabolic pathways. Extreme oxidative stress is associated with the trigger to fibrosis generation; therefore if redox homeostasis is re-established, down-regulation of the fibrogenic process may be achieved. The medical food of the present invention's intended use is to re-establish redox homeostasis by fulfilling the metabolic/nutritional demands of the CLD patients. Studies have shown that once the fibrogenic activity is eliminated, resorption of hepatic collagen may then occur thereby decreasing fibrosis staging.

The Present Medical Food Invention Fulfills the New Distinctive Nutritional Requirements of CLD Patients Present Invention Supplies Metabolites Involved in Glutathione (GSH) Biosynthesis Glutathione (GSH) in the body is intrinsically involved with cellular redox homeostasis, and therefore GSH homeostasis is important in any disease that causes increased levels of oxidative stress. As noted previously, extreme oxidative stress is a hallmark of CLD and GSH is depleted due to decreased production and overconsumption. Also, GSH experiences decreased production in CLD due to CMP disruption of the SAMe cycle and one-carbon metabolism. Therefore, researchers have called for studies that investigate the administration of precursor metabolites of GSH synthesis to patients with diseases associated with metabolic depletion of GSH, describing it as a step that is important for research efforts into a variety of chronic diseases.

GSH is essential for cellular redox homeostasis and GSH synthesis is tightly regulated in the cytosol. After synthesis, GSH is distributed to intracellular compartments such as the mitochondrial membrane, endoplasmic reticulum and the nucleus. It is also exported to extracellular spaces including the blood and bile for utilization by other tissues. The half-life of GSH is only 2-3 hours. GSH is only catabolized in the extracellular space by gamma-glutamyl transferase (GGT). The gamma glutamyl cycle involves the rapid catabolism of extracellular GSH into constituent peptides, which are then quickly taken back up by the cells for rapid re-synthesis into GSH. This gamma glutamyl cycle of GSH cellular export/catabolism/re-uptake/re-synthesis may be energy inefficient, but it is a perfect design for a rapid-response antioxidant system in response to extreme oxidative challenges. Intracellular GSH status depends on precursor availability, the rate of GSH oxidation to GSSG, and the capacity to recycle GSSG back to GSH at the expense of NADPH. Under normal physiological conditions, reduced GSH levels are 10 to 100 times greater than oxidized GSH (GSSG) and mixed disulphide (GSSR). The ratio of reduced and oxidized forms of GSH is important in cell signaling, maintaining redox homeostasis and the promotion of cellular mechanisms associated with cell proliferation, cell differentiation or apoptosis, while small variations in GSH:GSSG ratio tightly regulate redox signaling.

GSH depletion has been associated with inhibition of cytochrome c oxidase (CcOX) activity, microtubule network disassembly, and processes associated with NO toxicity.

In GSH biosynthesis, GSH is produced through the transsulfuration pathway involving SAMe conversion (cycling) to homocysteine, then to NAC. NAC and L-Glutamate are then combined into gamma-glutamylcysteine by the enzyme gamma-glutamyl synthetase—the rate-limiting step in the biosynthesis of GSH. Glycine is then added to the C terminal of the gamma-glutamylcysteine molecule by the action of the enzyme glutathione synthetase.

CMP-associated oxidative stress induced by CLD increases GSH activity and consumption, which in turn prompts changes in GSH levels. CLD creates a distinctive nutritional requirement for increased GSH production. As noted above, GSH is depleted in CLD, causing demand for greater synthesis and flux of SAMe and other GSH metabolites through the GSH pathway. GSH depletion has been shown to be involved in hepatic stellate cell activation in fibrogenesis.

GSH performs a variety of metabolic roles in the body, including antioxidant functions as a radical scavenger and as a redox signaling modulator. GSH scavenges free radical ROS and RNS directly and indirectly through enzymatic reactions. GSH also reacts enzymatically with hydroperoxides, being a co-substrate for selenium-dependent Glutathione Peroxidase (GPX), which is the body's most important mechanism for reducing $H_2O_2$ and lipid hydroperoxides. GSH may also reduce and detoxify ROS-promoted lipid-oxidation products such as malonyl dialdehyde and 4-hydroxy-2-nonenal, as well as many other species. GSH maintains thiol homeostasis of cysteine residues on proteins. It also conjugates and stores cysteine reserves. Glutathione is associated with estrogen, leukotriene, and prostaglandin metabolism. GSH also participates in the production of deoxyribonucleotides, in the maturation of iron-sulfur cluster in proteins, and it participates in signal transduction and cellular transcription.

As noted previously, the medical food has chosen to include NAC to increase GSH production rather than SAMe. Administration of NAC has also long been known to safely promote intracellular GSH production, decrease oxidative stress and has had anti-fibrotic actions in preliminary human studies. NAC has also been shown to decrease inflammatory markers and decrease hepatic fatty acid accumulation in ethanol-fed rats. The addition of NAC to corticosteroids has also been shown to decrease hepatorenal syndrome, infection, and short-term mortality in patients with severe ALD.

The medical food supplies NAC for GSH synthesis, which decreases demand for SAMe because SAMe is normally converted to NAC for GSH synthesis. As stated previously, the present invention also provides PC, which also decreases SAMe utilization in the PC PEMT biosynthetic pathway in CLD. Administration of NAC and PC, both of which are metabolic end-products of CMP-disrupted metabolic pathways, conserve SAMe for other purposes, including DNA methylation or some of the many other metabolic functions of SAMe.

CLD is associated with DNA hypomethylation. DNA hypomethylation results in phenotypic and epigenetic alterations. ALD causes alcoholic steatosis and methionine metabolism disruption associated with DNA hypomethylation and altered gene expression. SAMe is one of the main one-carbon methyl donors that methylates DNA. However, SAMe availability is limited by impaired enzyme activity in the SAM/SAH/methionine cycle in ALD patients, and decreased SAMe is one of the causes of DNA hypomethylation. The medical food restores SAMe availability by administering all of the one-carbon methyl donors associated with CMP pathways, as well as by saving SAMe from overutilization in the GSH and PC pathways. In this way, the medical food's one-carbon metabolites safely restore enzymatic cycling of the homocysteine/SAH/methionine pathway to produce more SAMe for proper DNA methylation.

CLD is also characterized by increased mitochondrial permeability transition, and this is associated with ROS penetration into the cytosol. NAC has been shown to inhibit alterations of mitochondrial permeability transition. Therefore, metabolic precursors of the GSH biosynthetic pathway including NAC, glycine, and glutamate are the distinctive required nutrients for patients with CLD.

The Present Invention Supplies Metabolites Involved in Other GSH-Interlinked Antioxidant Systems New distinctive nutritional requirements created by CLD necessitate systematic and comprehensive dietary management. A 1997 review regarding viral diseases and their induction of oxidative stress remarked how complex and deleterious the pathogenic induction of oxidative stress is, noting that supplying specific antioxidants may solve both short-term and long-term issues seen in patients with HCV.

GSH biosynthesis is intrinsically involved in the regulation and redox cycling of various antioxidant systems. In particular, CMP up-regulated thiol-containing antioxidant systems need dietary management to fulfill their functions and remain in homeostasis, and the medical food supplies NAC, ALA and PC to fulfill the distinctive nutritional requirement of CLD patients for these up-regulated thiols.

The body has two basic antioxidant systems, classified as the enzymatic antioxidant system and the non-enzymatic antioxidant system:

Enzymatic antioxidants include superoxide dismutase (SOD), catalase, glutathione peroxidase, thioredoxin and glutaredoxin.

Small molecule non-enzymatic antioxidants include lipid soluble vitamins A, D and E. Vitamins B, C and GSH are water-soluble antioxidants. GSH is the master controller for proper cooperative reduction of these linked-chain small molecule non-enzymatic cellular antioxidants.

Intracellular small molecule antioxidants like vitamins B's, C, D and E are consumed at an increased rate due to CLD-associated extreme oxidative stress. In addition, trace elements like zinc, selenium, and manganese are metabolic antioxidant cofactors that also experience greater utilization in patients with CLD. Selenium is a cofactor of glutathione peroxidase and zinc, manganese and copper are cofactors for SOD.

These small molecule antioxidants require reduction after oxidation in order to re-establish antioxidant function. This is accomplished through reducing systems such as glutathione/glutathione disulfide, dihydrolipoate/lipoate, or NADPH/NADP+ and NADH/NAD+. These small molecule antioxidants also reduce each other in a linked-chain re-charging redox system. For instance, CoQ10 has been shown to enhance enzymatic NADH- and NADPH-recycling of tocopherols in mitochondria without being consumed itself. Vitamin C, ALA and GSH all reduce vitamin E. Vitamin E reduces vitamin A and the carotenoids, while it stabilizes membranes and protects against lipid peroxidation. ALA and selenium reduce GSH. GSH reduces cystine, vitamin C and polyphenols. Decreased levels of GSH and increased oxidative stress associated with CLD have an impact on the reduction capacity of the small-molecule non-enzymatic antioxidant system, while chronic extreme oxidative stress may impair the ability of the redox system to maintain cellular redox homeostasis. Due to the interlinked nature of their redox duties, depletion of any individual members of this cellular non-enzymatic small-molecule antioxidant recharging system may result in decreased levels of all members of this linked antioxidant system. For these reasons, proper combinations of linked antioxidants are required for full-system stabilization. GSH also contributes to the redox homeostasis of mitochondrial antioxidant metabolites, including the B vitamin family, CoQ10 and ALA.

Antioxidant minerals such as zinc, selenium and magnesium are consumed at a higher rate in CLD related to increased oxidative stress. ALD has also been shown to impair zinc uptake. Therefore, CLD creates a distinct nutritional requirement for increased intake of these antioxidant mineral metabolites. Zinc, selenium and magnesium are part of the required nutrients contained in the medical food to meet increased demand from CLD-associated elevation of oxidative stress.

The medical food contemplated herein provides the full complement of interlinked small-molecule non-enzymatic antioxidants, including the antioxidant minerals zinc, selenium, magnesium, CoQ10, vitamins A, B, C, D, E, and the thiol-based cellular antioxidant ALA in moderate, balanced quantities. The medical food's three times-daily administration schedule is intended to maximize periods of nutrient delivery in response to the constant up-regulated metabolic and nutritional demands of patients with CLD.

The medical food nutrients also fulfill a distinctive nutritional requirement for B vitamins, which are necessary for proper mitochondrial metabolism, and which are altered in CLD. Vitamin B deficiencies cause mitochondrial dysfunction, and administration of B vitamins may ameliorate symptoms associated with B vitamins deficiencies and prevent mitochondrial toxicity ( ).

The medical food fulfills a distinctive nutritional requirement for all the B vitamins in patients with CLD. This distinctive nutritional requirement is due to increased consumption due to CLD-associated extreme oxidative stress. Niacin (vitamin B3) is a necessary mitochondrial B vitamin and is the precursor of NAD and NADPH. Niacin supplementation has a positive effect on fatty liver. A study by Li et al found "Chronic EtOH feeding induced significant lipid accumulation in the liver, which was . . . ameliorated by dietary NA supplementation. Liver total NAD, NAD(+), and NADH levels were remarkably higher in the NA supplemented group than the NA deficient or EtOH alone groups". NADH reduces oxidized GSH. The medical food supplies thiamine (vitamin B1), another mitochondrial antioxidant B vitamin found decreased in CLD. Thiamine administration reversed many of the detrimental effects of ethanol administration in rats.

Studies showed HCV creates a distinctive nutritional requirement for increased CoQ10 due to HCV-induced depletion of mitochondrial GSH, increase in ROS production and disruption of the mitochondrial electron transport chain. CoQ10 is a mitochondrial antioxidant and involved in electron transport in the mitochondria, Intracellular CoQ10 levels reflect the functional status of the electron transport complex in the mitochondria. CoQ10 reduces GSH without being consumed itself due to its promotion of enzymatic process.

The medical food formula fulfills the distinctive nutritional requirements for vitamin E, selenium, magnesium and zinc, which are depleted in CLD, in particular HCV infection. Studies demonstrated administration of these antioxidants alleviated symptoms of oxidative stress in patients with HCV.

The medical food also fulfills a distinctive nutritional requirement for magnesium. Magnesium deficiency is associated with cirrhosis and it plays a significant role in increasing oxidative stress and apoptosis, as well as accelerating the aging process. Zinc has long been known to have antioxidant functions. As noted above, various studies found selenium and zinc at low levels in CLD and HCV-infected patients. Zinc and selenium were also found to be decreased in liver cirrhosis patients, and administration of zinc and selenium had positive metabolic effects on cirrhotic and cancer patients. Vitamin E and selenium were found to promote hepatic stellate cell apoptosis in rats. Selenium has long been known for its antioxidant effects, and studies show that selenium appears to cause up-regulation of manganese superoxide dismutase (MnSOD). Selenium is also involved in the thioredoxin and glutaredoxin thiol-based enzymatic antioxidant systems. Vitamin E and selenium supplied together have been found to decrease hepatic stellate cell activation and hepatic fibrosis.

Vitamin D is a metabolic antioxidant, and it is known to be deficient in all CLD, in particular NAFLD and HCV. The medical food nutrients fulfill a distinctive nutritional requirement for Vitamin D in CLD patients.

The medical food nutrients fulfill a distinctive nutritional requirement for alpha lipoic acid (ALA), which is a cellular thiol-containing antioxidant ALA can lower oxidative stress and it plays an essential role in mitochondrial antioxidant reactions, quenching ROS such as superoxide radicals, hydroxyl radicals, hypochlorous acid, peroxyl radicals, and singlet oxygen. ALA also reduces vitamin C and GSH, which in turn recycles vitamin E. ALA fulfills a requisite distinctive nutritional need because of the role that ALA plays in CMP-altered metabolic systems, especially in CMP-altered cellular redox homeostasis. ALA directly scavenges ROS, but it also recycles other antioxidants like GSH and vitamin C and prevents toxicities associated with their depletion. ALA promotes GSH synthesis and vitamin C levels, and modulates transcription factors like NFkappaB. Studies show ALA has dramatic effects in oxidative stress conditions. L-carnitine and ALA reversed mitochondrial oxidative damage and serum liver enzymes in NASH model mice. Further, ALA chelates metal ions like iron and copper.

ALA is an important constituent of the linked-chain intracellular antioxidant system and it is known to have potent redox properties, but evidence shows that besides being a direct scavenger of oxidants, ALA has been shown to stimulate GSH synthesis through an up-regulation of a transcription factor, Nrf2. Nrf2 determines the expression of antioxidant and detoxification genes regulated by the antioxidant response element (ARE). Significantly, ALA has also been shown to modulate NF-kappaB transcription factor activity, which is involved in hepatic stellate cell activation.

CLD-induced oxidative stress establishes the distinctive nutritional requirement for thiol-containing antioxidants as well as non-enzymatic small molecule cellular antioxidants, of which ALA is both. The medical food medical food protocol provides moderate amounts of ALA to fulfill the distinctive nutritional requirements of CLD patients.

The Medical Food of the Present Invention Supplies Botanical Polyphenols—Integral Components of the Body's Physiological Antioxidant Response The medical food provides polyphenols from GRAS botanicals due to the new distinctive nutritional requirements of CLD patients and their CMP-associated disruption of redox system homeostasis and inducement of extreme oxidative stress. Polyphenols from GRAS botanicals are important integral components of the body's normal metabolic response to oxidative stress. Studies have shown that botanical polyphenols prevent Nrf2 translocation and modulate NF-kappaB pathways, thereby protect DNA from oxidative stress-mediated damage. Dietary botanical polyphenols are integral components of our bodies' physiological antioxidant response. Administration of botanical polyphenols and other antioxidant metabolites have been shown to be helpful in liver disease due to their metabolic antioxidant effects.

The medical food provides the following GRAS botanicals whose administration in animal and human studies on CMP-associated oxidative stress have been demonstrated:

*Artimisia absinthia* (wormwood) has been shown to prevent chemically induced liver damage in animal models. *Artimisia* has also been shown to be hepatoprotective in ethanol-induced hepatotoxicity in animal models and antifibrotic in CCl4 induced fibrosis in animal models. *Artimisia* inhibited the inflammatory response induced by lipopolysaccharides by preventing NF-kappaB activation in human hepatoma cells and rat livers.

*Piper cubeba* (cubeb berries) has been used in folk medicine for centuries. It contains monoterpenes and sesquiterpenes among its phenolic components while also providing micronutrients. *Piper* also contains piperine, which has been associated with antioxidant efficacy, inhibition of liver fibrosis and hypolipidic effects in high-fat diet rats. Piperine has also been shown to inhibit the macrophage inflammatory response.

*Cynara scolymus* (artichoke) has been shown to reduce hepatic oxidative stress and restore lipoprotein homeostasis in rats fed a high cholesterol diet. Polyphenols from artichoke have been shown to markedly reduce hepatic oxidative stress in rats and to prevent the loss of GSH in rat hepatocytes. Further, artichoke was found to inhibit cholesterol biosynthesis in rat hepatocytes. As seen in Part A, cholesterol levels increase in patients with CLD due to CMP-associated metabolic changes.

*Nigella sativa* (black cumin) administration to HCV patients in Egypt was found to be " . . . tolerable, safe, decreased viral load, and improved oxidative stress, clinical condition and glycemic control in diabetic patients". Black cumin seeds and oils have been found to be hepatoprotective against hepatotoxicity induced by either disease or chemicals. The beneficial effects are likely related to their cytoprotective and metabolic antioxidant actions. In lipopolysaccharide-induced inflammation, black cumin has an antioxidant effect. Black cumin has also been shown to have beneficial immunomodulatory properties related to its metabolic antioxidant properties.

*Curcuma longa* (Turmeric) has been found to have significant hepatic antioxidant properties in ethanol-induced oxidative stress, in rabbits fed an atherogenic diet, and in liver oxidative damage induced by lead acetate in mice. Turmeric extract (curcumin) has been found to inhibit the progression of liver cirrhosis in thiocetamide induced liver cirrhosis in rats. Turmeric extract was also found to regulate plasma cholesterol and fatty liver in rats fed a high-cholesterol diet Turmeric exerts an antioxidative effect on phospholipid peroxidation and hepatic lipid metabolism in mice fed a high cholesterol or atherogenic diet Curcumin has long been shown to be an effective antioxidant nutrient in liver diseases. Further, Curcumin inhibits several factors like nuclear factor NF-kappaB, a prototypical proinflammatory signaling pathway. Curcumin attenuates liver injury induced by ethanol, thioacetamide, iron overdose, cholestasis and acute, subchronic and chronic carbon tetrachloride (CCl(4)) intoxication. Moreover, curcumin reverses CCl (4) induced cirrhosis. Curcumin has been shown to be hepatoprotective against ethanol-induced hepatic fibrosis by inhibiting hepatic stellate cell proliferation and by suppressing TGF-Beta signaling.

Grape Seed extract has been shown to reduce oxidative stress in experimental animal biliary obstruction studies, in methotrexate induced oxidative stress in rat liver, in radiation induced oxidative stress in rat liver, and in a rat model of diabetes mellitus, which is a condition that aggravates CLD. Grape Seed extract has also been shown to improve liver function in patients with NAFLD.

The Medical Food of the Present Invention Supplies Phosphatidylcholine (PC), Which Fulfills a Distinctive Nutritional Requirement for Increased PC in Chronic Liver Disease Patients A recent review summarized current and historical in-vitro and clinical studies on PC. The animal studies and in-vitro studies reviewed in the analysis found that, " . . . EPL influenced membrane-dependent cellular functions and showed anti-oxidant, anti-inflammatory, anti-fibrotic, apoptosis-modulating, regenerative, membrane-repairing and -protective, cell-signaling and receptor influencing, as well as lipid-regulating effects in intoxication models with chemicals or drugs." The review also analyzed clinical studies, where patients with CLD of all etiologies, " . . . have shown improvement in subjective symptoms; clinical, biochemical and imaging findings; and histology in liver indications such as fatty liver of different origin, drug hepatotoxicity, and adjuvant in chronic viral hepatitis and hepatic coma.

PC is a main cellular membrane phosphoplipid, and it is associated with proper cell membrane and mitochondrial membrane form and function. PC is synthesized in two different biosynthetic pathways in the body. These include the SAMe dependent PEMT pathway and CDP-choline pathway. In the PEMT pathway, SAMe is involved in three successive methylations of phosphatidylethanolamine (PE) to form PC. The PEMT pathway occurs in the liver only. The other main PC biosynthetic pathway is called the CDP-choline pathway (or the Kennedy pathway) and it occurs in the rest of the cells of the body. In this pathway, PC is created through conversion of dietary choline into CDP-choline and then to PC.

CLD causes decreased availability of PC, and oxidation of PC in membranes can occur in CLD due to extreme oxidative stress. It has been shown that CLD creates increased demand for PC and choline. The medical food supplies PC, the biosynthetic end-product of both PC pathways. PC administration spares SAMe from increased flux into the PEMT PC pathway. PC administration also produces choline, which is produced from the catabolism of PC. Both dietary choline and PC-derived choline are either cycled back to the CDP-choline pathway for PC production or cycled to the production of betaine, a necessary one-carbon donor involved in the SAM/SAH/methionine metabolism, or also to acetylcholine.

Choline regulates cholesterol metabolism, which is another up-regulated CMP-associated pathway. Choline supplementation improved liver function and prevented NASH in a study on PEMT knockout mice. As reported by Al Rajabi et al, hepatic cholesterol but not triglyceride was normalized with a significant improvement in liver function when supplemented with choline. They concluded that their findings suggested choline can maintain cholesterol homeostasis and thereby promote liver health.

Dr. Lieber found that oral supplementation of PC caused increased GSH synthesis due to increased SAMe availability. This increase in SAMe stores was due to decreased metabolic demand for SAMe into the PEMT pathway due to PC end-product supplementation. Dr. Leiber surmised, " . . . it is likely that . . . providing PCs, decreases the utilization of SAMe and thereby contributes to its restoration, with replenishment of GSH and correction of the alcohol-induced oxidative stress".

The Lieber study above showed that PC supplementation decreases flux of SAMe from the PC biosynthetic pathway to the GSH biosynthetic pathway. It is also true that the flux of SAMe may be decreased into the CMP up-regulated GSH biosynthetic pathway if that pathway is supplied with additional amounts of NAC. NAC and SAMe are the two rate-limiting metabolites in GSH biosynthesis, and either will promote the production of GSH. NAC has been shown to decrease oxidative stress in alcoholic hepatitis and in cirrhosis animal studies.

Interestingly, PC administration by itself has shown an anti-fibrogenic effect in studies performed on patients with CLD. A European PC clinical study found reduced levels of procollagen-III-peptide in HBV patients, while a study on HCV patients found decreased levels of albumin-bound hydroxyproline. Remarkably, anti-fibrotic improvement in histology was shown in pharmacological and clinical studies performed on patients and animals administered PC.

The Medical Food of the Present Invention Supplies Metabolites of the SAM/SAH/Methionine Cycles, Which Experience Greater Utilization by Chronic Liver Disease Patients Studies showed SAMe has positive effects on oxidative stress in CLD, increasing GSH levels, which are depleted in CLD. It is known that SAMe may play an important role in reversing hepatic glutathione depletion in patients with CLD. While the medical food does not supply SAMe, it supplies the other rate limiting metabolite of GSH synthesis, NAC, for GSH synthesis instead. Supplying NAC decreases demand for SAMe in the GSH biosynthetic loop because SAMe is converted to NAC for GSH synthesis. The medical food also supplies PC to the CMP up-regulated PC pathway; thus, decreasing flux of SAMe into the PC pathway. Both of these actions free up potential SAMe stores for DNA methylation or the many other biosynthetic functions of SAMe.

A 1989 study showed that SAMe increases hepatic GSH in patients with liver disease. In an ethanol-induced fibrotic mouse model, SAMe administration was shown to attenuate oxidative stress and hepatic stellate cell activation. SAM/SAH/methionine cycling has been shown to be impaired in CLD and administration of one-carbon metabolites have been shown to restore proper cycling, see Section 5 below. Thus, the medical food contemplated herein fulfills the distinctive nutritional requirements for increased SAMe and one-carbon metabolites for proper Sam/SAH/methionine cycling.

Methionine/homocysteine metabolism and choline metabolism are interdependent Choline is recycled from catabolized PC and is converted mainly back to PC, but also to acetylcholine and betaine. Feeding a diet deficient in choline and methionine has been used as a mechanism to create steatosis in the lab for studies. As noted previously, all of these CLD-affected pathways are linked to SAM/SAH/methionine and GSH metabolism, and therefore nutritional deficiencies in any of these pathways may contribute to oxidative stress.

The Medical Food of the Present Invention Supplies Metabolites of One-Carbon Methyl Metabolism The medical food formula also includes one-carbon methyl donors such as folate, vitamin B12, vitamin B6 and betaine. Increased SAM/SAH/methionine cycling creates greater demand for one-carbon methylation factors. These one-carbon metabolites are distinctive required nutrients provided in the medical food medical food protocol for their one-carbon methyl donating properties and their interlinked duties with the SAM/SAH/methionine cycle and the homocysteine/NAC/GSH cycle, both of which experience greater utilization in patients with CLD.

One-carbon methyl donors like folate, vitamin B12 and betaine convert homocysteine to methionine, and vitamin B6 directs homocysteine to NAC, which is then ultimately converted to GSH. Proper methylation by these one-carbon methyl donors is important to avoid accumulation of homocysteine in the body. Therefore, any up-regulation of the SAM/SAH/methionine cycle must necessarily be accompanied by increased utilization of these critical one-carbon methyl donors.

A study showed that ALD patients experience decreased folate, vitamin B6 and thiamine levels, suggesting that these deficiencies were due to the patients' inability to absorb those vitamins from food. Interestingly, these patients were able to absorb synthesized supplemental forms of these vitamins, in spite of their inability to absorb the nutrients from food. Another study showed Thiamine supplementation reversed ethanol-induced hepatotoxicity in rats.

Betaine, one of a necessary medical food metabolites, aids in the conversion of homocysteine to methionine. Betaine is also a thiol-enhancing cofactor.

One-carbon methyl donors have positive nutritional effects on redox homeostasis and oxidative stress due to their intrinsic role in SAM/SAH/methionine metabolism. As noted previously, the medical food does not provide SAMe or methionine to satisfy the distinctive nutritional requirement of CLD patients for increased SAMe. Rather, the medical food concentrates on saving SAMe by decreasing the draw of SAMe into the other highly up-regulated CMP pathways, the PC and GSH pathways. Further, SAMe-homocysteine-methionine cycling is impaired due to decreased enzymatic activity, which the medical food restores by administering one-carbon metabolic methyl donors like betaine, which protects against ethanol-induce fatty liver infiltration in ALD. Betaine's restorative powers to disrupted ALD metabolic pathways is generally attributed to its role in restoring SAMe supplies and thereby decreasing oxidative stress. A study conducted by Yung et al documented, that betaine's hepatoprotective activity is associated with its effects on sulfur amino acid metabolism.

The Medical Food of the Present Invention Supplies Metabolites of CLD-Depleted Amino Acid Metabolism CLD increases utilization and decreases availability of L-Carnitine. L-Carnitine levels are diminished in all CLD, in particular HCV, and this makes it a required metabolite in the medical food medical food formula. Depletion of L-Carnitine may have negative effects on CLD-associated steatosis because L-Carnitine transports cytosolic fatty acids to the mitochondria for β-oxidation. β-oxidation of fatty acids is another CMP up-regulated activity. The medical food supplies L-lysine, which combines with methionine to form the CMP-depleted amino acid, L-Carnitine. The medical food also supplies L-Carnitine to meet increased demands for increased β-oxidation of fatty acids in patients with CLD. In a NASH mouse model, "L-Carnitine prevents progression of NASH in a mouse model by up-regulating the mitochondrial β-oxidation and redox system". L-Carnitine and ALA reversed mitochondrial oxidative damage and serum liver enzymes in NASH mouse model.

The medical food also supplies arginine as a required amino acid metabolite in CLD patients. Arginine is oxidized to form nitric oxide (NO). NO is involved in the modulation of hepatic microcirculatory perfusion and oxygenation in cholesterol-induced hepatic steatosis. Arginine administration selectively increases NO levels, which improves hepatic microcirculation and tissue oxygenation in patients with cirrhosis. A study conducted by Nanji et al reported that " . . . our results show that arginine administration, probably through the generation of nitric oxide, leads to improvement in pathological changes such as fatty liver, necrosis, inflammation, and fibrosis. These improvements were accompanied by down-regulation of nuclear factor NF-κB, pro-inflammatory cytokines cyclooxygenase-2, and inducible nitric oxide synthase". GSH depletion leads to NO toxicity, so the medical food contemplated herein supplies the GSH metabolites NAC, L-glutamate and L-lysine for GSH production.

The medical food supplies arginine as a necessary amino acid metabolite for patients with CLD. Decreased arginine levels may be associated with hepatic encephalopathy and hyperammonemia due to urea cycle disruption. Studies have found that the CMP-associated metabolic disruption of the of ammonia detoxification pathway, " . . . preceed the histological manifestation of irreversible liver damage". Arginine administration must be balanced with lysine administration, which is also present in the medical food formula. Lysine is also a metabolic precursor of L-carnitine, as mentioned above.

Exemplary Composition Embodiments

In a particular embodiment, a daily dose of the medical food contemplated herein may comprise the following ingredients in the following mass ranges:

L-Lysine in a range of 400-5,000 mg
N-Acetyl Cysteine in a range of 500-5,000 mg
L-Arginine in a range of 1,000-9,000 mg
Polyenylphosphatidylcholine in a range of 500-10,000 mg
Alpha Lipoic Acid in a range of 200-2,500 mg
Vitamin C (as ascorbic acid & calcium ascorbate) in a range of 500-10,000 mg
N-Acetyl L-Carnitine in a range of 250-3,000 mg
Betaine HCl in a range of 300-20,000 mg
L-Glutamate in a range of 200-2,000 mg
Turmeric (*Curcuma longa*) in a range of 200-1,500 mg
Grape seed extract (95% Proanthocyanidins) in a range of 100-1,000 mg
Black cumin seed (*Nigella sativa*) in a range of 50-400 mg
Pantothenic acid (as calcium pantothenate) in a range of 20-10,000 mg
Benfotiamine in a range of 50-400 mg Magnesium (as magnesium citrate) in a range of 50-800 mg
Vitamin E (as mixed tocopherols) in a range of 50-1,000 IU
Artichoke (leaf) extract (*Cynara scolymus*) in a range of 25-300 mg
L-Glycine in a range of 50-3000 mg
Vitamin B1 in a range of 10-200 mg
Vitamin B2 in a range of 10-200 mg
CoQ10 (as ubiquinol) in a range of 30-1,000 mg
Cubeb berries (*Piper cubeba*) in a range of 10-100 mg
Wormwood (*Artemisia absinthium*) in a range of 10-100 mg
Vitamin B3 in a range of 45-3,000 mg
Vitamin B6 (as pyridoxine HCl) in a range of 10-200 mg
Zinc (as zinc citrate) in a range of 5-50 mg
Vitamin D3 in a range of 400-10,000 IU
Folate (as folic acid) in a range of 200-3,000 mcg
Vitamin B12 (as methylcobalamin in a range of 200-3,000 mcg
Selenium (as selenate aspartate) in a range of 100-600 mcg
Biotin in a range of 50-2,000 mcg It should be understood that in varying embodiments, the present medical food may not have all of the above listed components. Indeed many may be omitted. In a particular embodiment, any combination of N-Acetyl Cysteine, Alpha Lipoic Acid, Polyenylphosphatidylcholine, and one or more of the above listed components may constitute the medical food of the present invention. In another embodiment, the medical food the composition may comprise Acetyl Cysteine, Alpha Lipoic Acid, Polyenylphosphatidylcholine.

In still another embodiment a daily dose of the medical food contemplated herein may comprise the following ingredients in the following mass ranges:
N-Acetyl Cysteine in a range of 500-5,000 mg
L-Arginine in a range of 1,000-9,000 mg
Polyenylphosphatidylcholine in a range of 500-10,000 mg
Alpha Lipoic Acid in a range of 200-2,500 mg Turning now to FIG. 1, a flow chart of an embodiment of use of the medical food of the present invention is provided. In this view, initially a patient having chronic liver disease is identified. This patient is then provided with a three times daily regimen of an embodiment of the medical food. The medical food may be taken in any number of manners, as noted above. After a period of time with taking the three times daily regimen of medical food, the patient may be tested to track progress and efficacy. This testing may involve any sort of sampling, including urine, blood, liver, fat, and/or tissue sampling, and the like. Based on the changes measured and caused by the medical food regimen, it may be adjusted, continued, or the like.

While several variations of the present invention have been illustrated by way of example in preferred or particular embodiments, it is apparent that further embodiments could be developed within the spirit and scope of the present invention, or the inventive concept thereof. However, it is to be expressly understood that such modifications and adaptations are within the spirit and scope of the present invention, and are inclusive, but not limited to the following appended claims as set forth.

What is claimed is:

1. A method of reversing liver fibrosis comprising the steps of administering a composition to a patient, the composition comprising:
    N-acetyl cysteine in a range of 500-5,000 mg;
    polyenylphosphatidylcholine in a range of 500-10,000 mg;
    alpha lipoic acid in a range of 200-2,500 mg; and
    at least one of: L-lysine in a range of 400-5,000 mg;
        L-arginine in a range of 1,000-9,000 mg; vitamin C in a range of 500-10,000 mg; N-acetyl L-carnitine in a range of 250-3,000 mg; betaine HCl in a range of 300-20,000 mg; L-glutamate in a range of 200-2,000 mg; turmeric in a range of 200-1,500 mg; proanthocyanidins in a range of 100-1,000 mg; *Nigella sativa* in a range of 50-400 mg; pantothenic acid in a range of 20-10,000 mg; benfotiamine in a range of 50-400 mg; magnesium in a range of 50-800 mg; vitamin E in a range of 50-1,000 IU; *Cynara scolymus* in a range of 25-300 mg; L-glycine in a range of 50-3000 mg; vitamin B1 in a range of 10-200 mg; vitamin B2 in a range of 10-200 mg; ubiquinol in a range of 30-1,000 mg; *Piper cubeba* in a range of 10-100 mg; *Artemisia absinthium* in a range of 10-100 mg; vitamin B3 in a range of 45-3,000 mg; vitamin B6 in a range of 10-200 mg; zinc in a range of 5-50 mg; vitamin D3 in a range of 400-10,000 IU; folate in a range of 200-3,000 mcg; vitamin B12 in a range of 200-3,000 mcg; selenium in a range of 100-600 mcg; and biotin in a range of 50-2,000 mcg;
    wherein the step of administering comprises dividing the composition into three equal doses, a first of the three doses administered at a first time, a second of the three doses administered at a second time, and a third of the three doses administered at a third time, the three doses administered in a 24 hour period;
    wherein the administering is repeated every 24 hours; and
    testing the patient, the step of testing comprising taking a sample from the patient, analyzing the sample for an indicator of liver fibrosis, and comparing the analyzed sample to a previously analyzed sample.

2. The method of claim 1 wherein the composition comprises each of:
    L-lysine in a range of 400-5,000 mg; L-arginine in a range of 1,000-9,000 mg; vitamin C in a range of 500-10,000 mg; N-acetyl L-carnitine in a range of 250-3,000 mg; betaine HCl in a range of 300-20,000 mg; L-glutamate in a range of 200-2,000 mg; turmeric in a range of 200-1,500 mg; proanthocyanidins in a range of 100-1,000 mg; *Nigella sativa* in a range of 50-400 mg; pantothenic acid in a range of 20-10,000 mg; benfotiamine in a range of 50-400 mg; magnesium in a range of 50-800 mg; vitamin E in a range of 50-1,000 IU; *Cynara scolymus* in a range of 25-300 mg; L-glycine in a range of 50-3000 mg; vitamin B1 in a range of 10-200 mg; vitamin B2 in a range of 10-200 mg; ubiquinol in a range of 30-1,000 mg; *Piper cubeba* in a range of 10-100 mg; *Artemisia absinthium* in a range of 10-100 mg; vitamin B3 in a range of 45-3,000 mg; vitamin B6 in a range of 10-200 mg; zinc in a range of 5-50 mg; vitamin D3 in a range of 400-10,000 IU; folate in a range of 200-3,000 mcg; vitamin B12 in a range 200-3,000 mcg; and selenium in a range of 100-600 mcg; and biotin in a range of 50-2,000 mcg.

3. The method of claim 1 further comprising the step of dividing the composition into a plurality of capsules, each of the plurality of capsules comprising a fraction of the composition.

4. The method of claim 1 wherein the testing is selected to analyze a rate of one carbon methylation metabolism which is supported by nutrients provided in the administration step.

5. The method of claim 1 wherein the testing is selected to analyze a rate of S-adenosyl methionine metabolism which is supported by nutrients provided in the administration step.

6. The method of claim 1 wherein the step of administration comprises administering a powdered composition.

7. The method of claim 6 further comprising the step of mixing the powdered composition with a food.

8. The method of claim 1 wherein the testing further comprises analyzing a metabolic marker.

9. The method of claim 8 wherein the metabolic marker is phosphatidylcholine homeostasis.

10. The method of claim 8 wherein the metabolic marker is a lysophosphatidylcholine species level.

11. The method of claim 1 wherein the composition is selected to reduce extreme oxidative stress caused by an altered nutritional requirement caused by chronic liver disease.

12. The method of claim 11 wherein the composition is selected to supply metabolites involved in glutathione biosynthesis.

13. The method of claim 1 wherein the composition is selected to provide a full complement of interlinked small-molecule non-enzymatic antioxidants, including the antioxidant minerals zinc, selenium, magnesium, CoQ10, vitamins A, B, C, D, E, and the thiol-based cellular antioxidant ALA.

14. The method of claim 1 further comprising the step of orally administering the composition.

15. A method of treatment for a patient having chronic liver disease comprising the steps of:
   identifying that the patient suffers from chronic liver disease based on a testing of a metabolic marker;
   administering a composition selected to reduce oxidative stress caused by an adjusted nutritional requirement caused by the chronic liver disease, the composition comprising:
   N-acetyl cysteine in a range of 500-5,000 mg;
   polyenylphosphatidylcholine in a range of 500-10,000 mg;
   alpha lipoic acid in a range of 200-2,500 mg; and
   at least one of: L-lysine in a range of 400-5,000 mg; L-arginine in a range of 1,000-9,000 mg; vitamin C in a range of 500-10,000 mg; N-acetyl L-carnitine in a range of 250-3,000 mg; betaine HCl in a range of 300-20,000 mg; L-glutamate in a range of 200-2,000 mg; turmeric in a range of 200-1,500 mg; proanthocyanidins in a range of 100-1,000 mg; *Nigella sativa* in a range of 50-400 mg; pantothenic acid in a range of 20-10,000 mg; benfotiamine in a range of 50-400 mg; magnesium in a range of 50-800 mg; vitamin E in a range of 50-1,000 IU; *Cynara scolymus* in a range of 25-300 mg; L-glycine in a range of 50-3000 mg; vitamin B1 in a range of 10-200 mg; vitamin B2 in a range of 10-200 mg; ubiquinol in a range of 30-1,000 mg; *Piper cubeba* in a range of 10-100 mg; *Artemisia absinthium* in a range of 10-100 mg; vitamin B3 in a range of 45-3,000 mg; vitamin B6 in a range of 10-200 mg; zinc in a range of 5-50 mg; vitamin D3 in a range of 400-10,000 IU; folate in a range of 200-3,000 mcg; vitamin B12 in a range of 200-3,000 mcg; selenium in a range of 100-600 mcg; and biotin in a range of 50-2,000 mcg;
   wherein the administering step is repeated every 24 hours; and
   testing the patient, the step of testing comprising taking a sample from the patient, analyzing the sample for the metabolic marker, and comparing the analyzed sample to a previously analyzed sample of the metabolic marker.

16. The method of claim 15 wherein the composition comprises each of:
   L-lysine in a range of 400-5,000 mg; L-arginine in a range of 1,000-9,000 mg; vitamin C in a range of 500-10,000 mg; N-acetyl L-carnitine in a range of 250-3,000 mg; betaine HCl in a range of 300-20,000 mg; L-glutamate in a range of 200-2,000 mg; turmeric in a range of 200-1,500 mg; proanthocyanidins in a range of 100-1,000 mg; *Nigella sativa* in a range of 50-400 mg; pantothenic acid in a range of 20-10,000 mg; benfotiamine in a range of 50-400 mg; Magnesium in a range of 50-800 mg; Vitamin E in a range of 50-1,000 IU; *Cynara scolymus* in a range of 25-300 mg; L-glycine in a range of 50-3000 mg; vitamin B1 in a range of 10-200 mg; vitamin B2 in a range of 10-200 mg; ubiquinol in a range of 30-1,000 mg; *Piper cubeba* in a range of 10-100 mg; *Artemisia absinthium* in a range of 10-100 mg; vitamin B3 in a range of 45-3,000 mg; vitamin B6 in a range of 10-200 mg; Zinc in a range of 5-50 mg; vitamin D3 in a range of 400-10,000 IU; folate in a range of 200-3,000 mcg; vitamin B12 in a range of 200-3,000 mcg; and selenium in a range of 100-600 mcg; and biotin in a range of 50-2,000 mcg.

17. The method of claim 15 wherein the metabolic marker is phosphatidylcholine homeostasis.

18. The method of claim 15 wherein the metabolic marker is a lysophosphatidylcholine species level.

19. The method of claim 15 wherein the composition is selected to supply metabolites involved in glutathione biosynthesis.

20. The method of claim 15 wherein the step of testing comprising taking a blood sample from the patient, analyzing the sample for appropriate liver function using blood tests, and comparing results of the analysis to a blood test from the patent analyzed before a first administration step.

* * * * *